(12) United States Patent
Sakaguchi et al.

(10) Patent No.: US 9,833,210 B2
(45) Date of Patent: Dec. 5, 2017

(54) MEDICAL IMAGE DIAGNOSTIC APPARATUS

(71) Applicants: Toshiba Medical Systems Corporation, Otawara-shi (JP); THE RESEARCH FOUNDATION FOR THE STATE UNIVERSITY OF NEW YORK, Amherst, NY (US)

(72) Inventors: Takuya Sakaguchi, Utsunomiya (JP); Yuichiro Watanabe, Yaita (JP); Hisato Takemoto, Amherst, NY (US); Daniel Bednarek, Cheektowaga, NY (US); Vijay Rana, Amherst, NY (US)

(73) Assignees: Toshiba Medical Systems Corporation, Otawara-shi (JP); The Research Foundation for the State University of New York, Amherst, NY (US)

( * ) Notice: Subject to any disclaimer, the term of this patent is extended or adjusted under 35 U.S.C. 154(b) by 140 days.

(21) Appl. No.: 14/809,586

(22) Filed: Jul. 27, 2015

(65) Prior Publication Data
US 2017/0027533 A1 Feb. 2, 2017

(51) Int. Cl.
*A61B 6/00* (2006.01)
(52) U.S. Cl.
CPC ............ *A61B 6/463* (2013.01); *A61B 6/5264* (2013.01); *A61B 6/544* (2013.01); *A61B 6/4441* (2013.01)

(58) Field of Classification Search
CPC ....... A61B 6/542; A61B 6/4233; A61B 6/465; A61B 6/461; A61B 6/54; A61B 6/547; G01N 23/04; G01N 2223/306; G01N 2223/3308
See application file for complete search history.

(56) References Cited

U.S. PATENT DOCUMENTS

2015/0139393 A1* 5/2015 Watanabe .............. A61B 6/542
378/62

FOREIGN PATENT DOCUMENTS

JP 2000-152924 A 6/2000
JP 2015-100416 A 6/2015

* cited by examiner

*Primary Examiner* — Hoon Song
(74) *Attorney, Agent, or Firm* — Oblon, McClelland, Maier & Neustadt, L.L.P.

(57) ABSTRACT

According to one embodiment, a medical image diagnostic apparatus includes an X-ray tube, X-ray detector, image generation circuitry, display, and correction circuitry. The X-ray tube generates X-rays to an object. The X-ray detector detects the X-rays. The image generation circuitry generate an X-ray image based on the detected X-rays. The display displays an incident dose of the X-rays on the object, on an object image indicating the object. The correction circuitry correct a relative positional relationship between the object image and a display area of the incident dose on the object image based on the X-ray image.

20 Claims, 12 Drawing Sheets

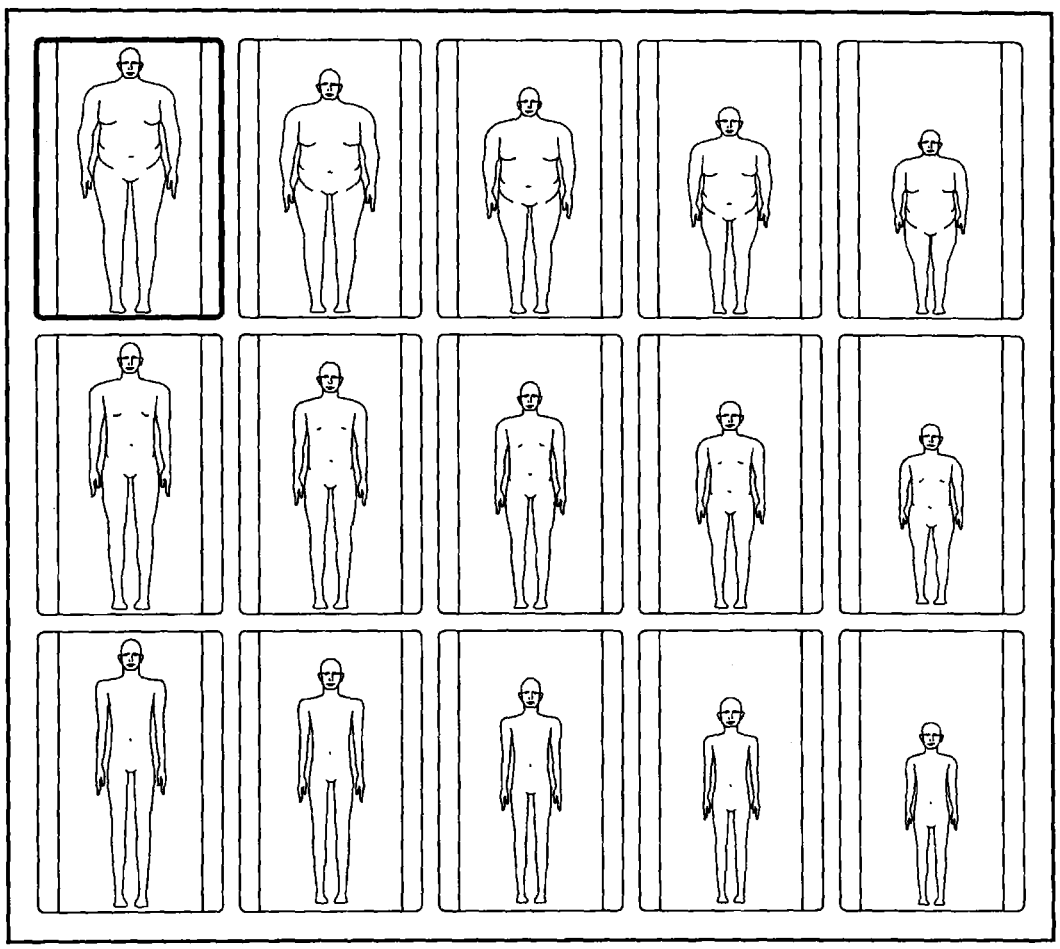
F I G. 2

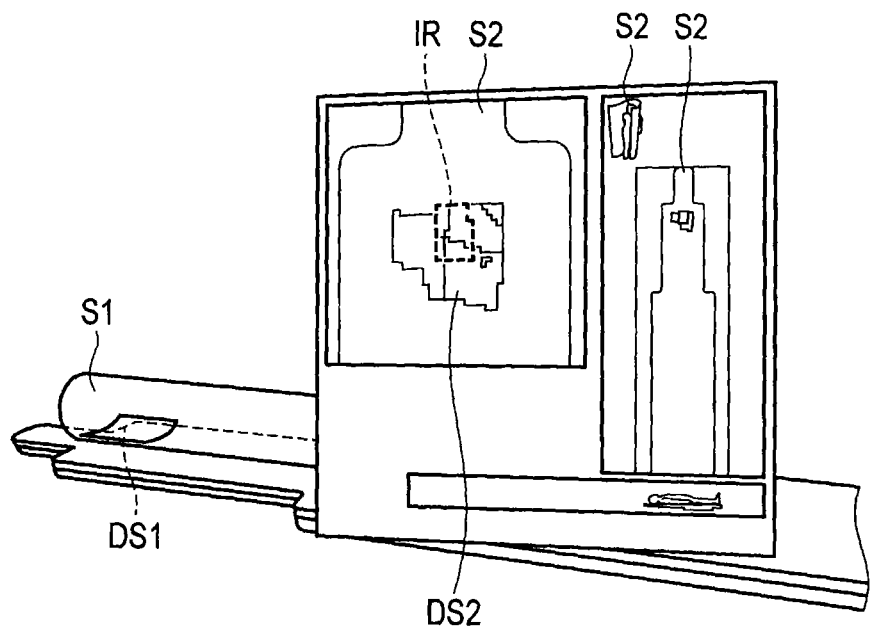
F I G. 3
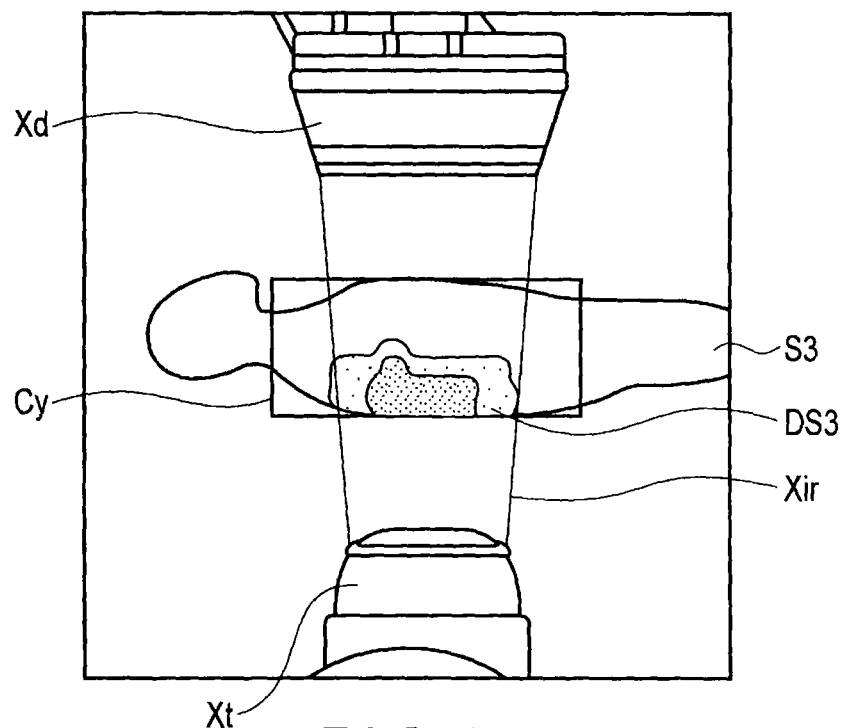
F I G. 4

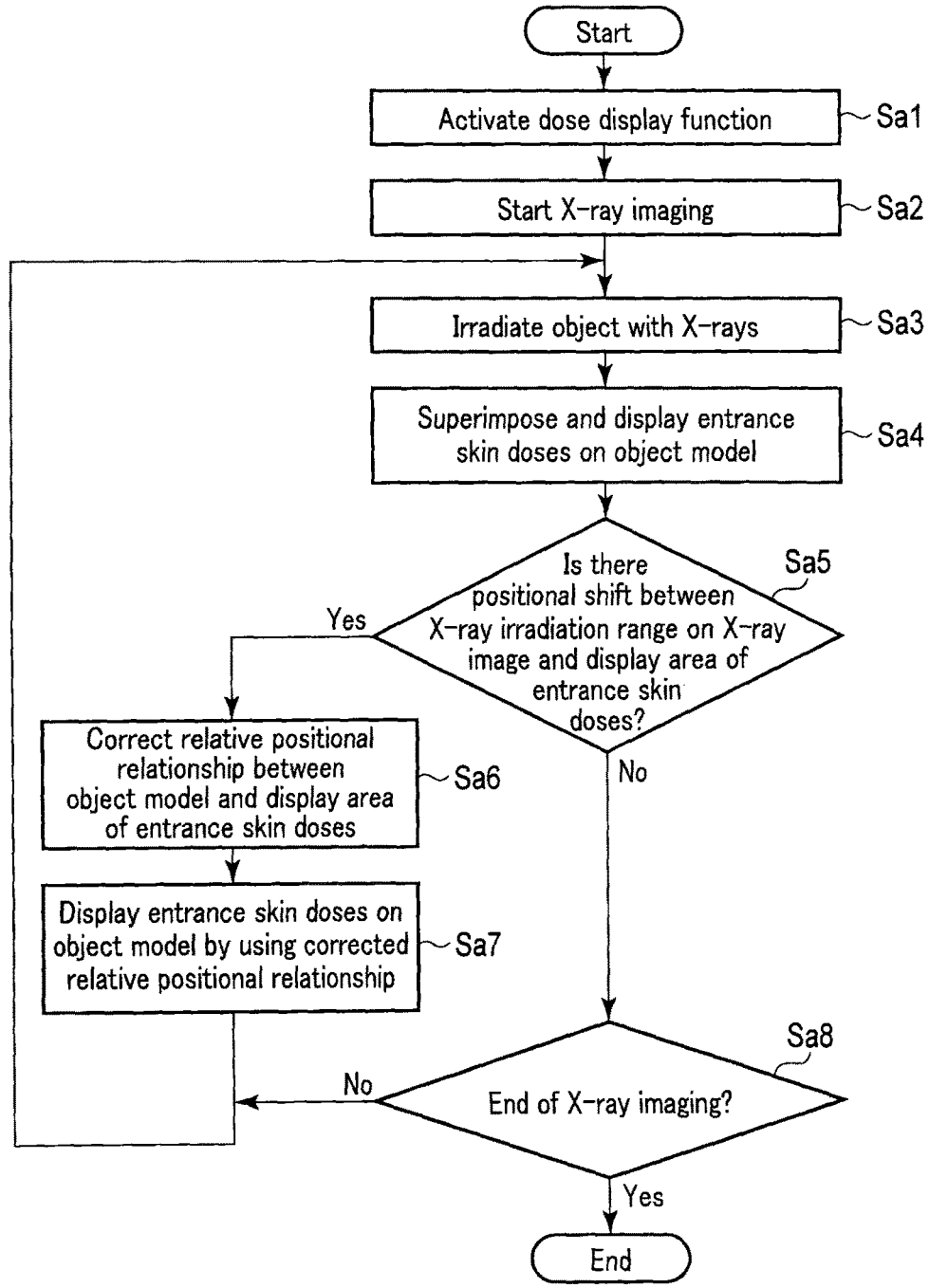
F I G. 6

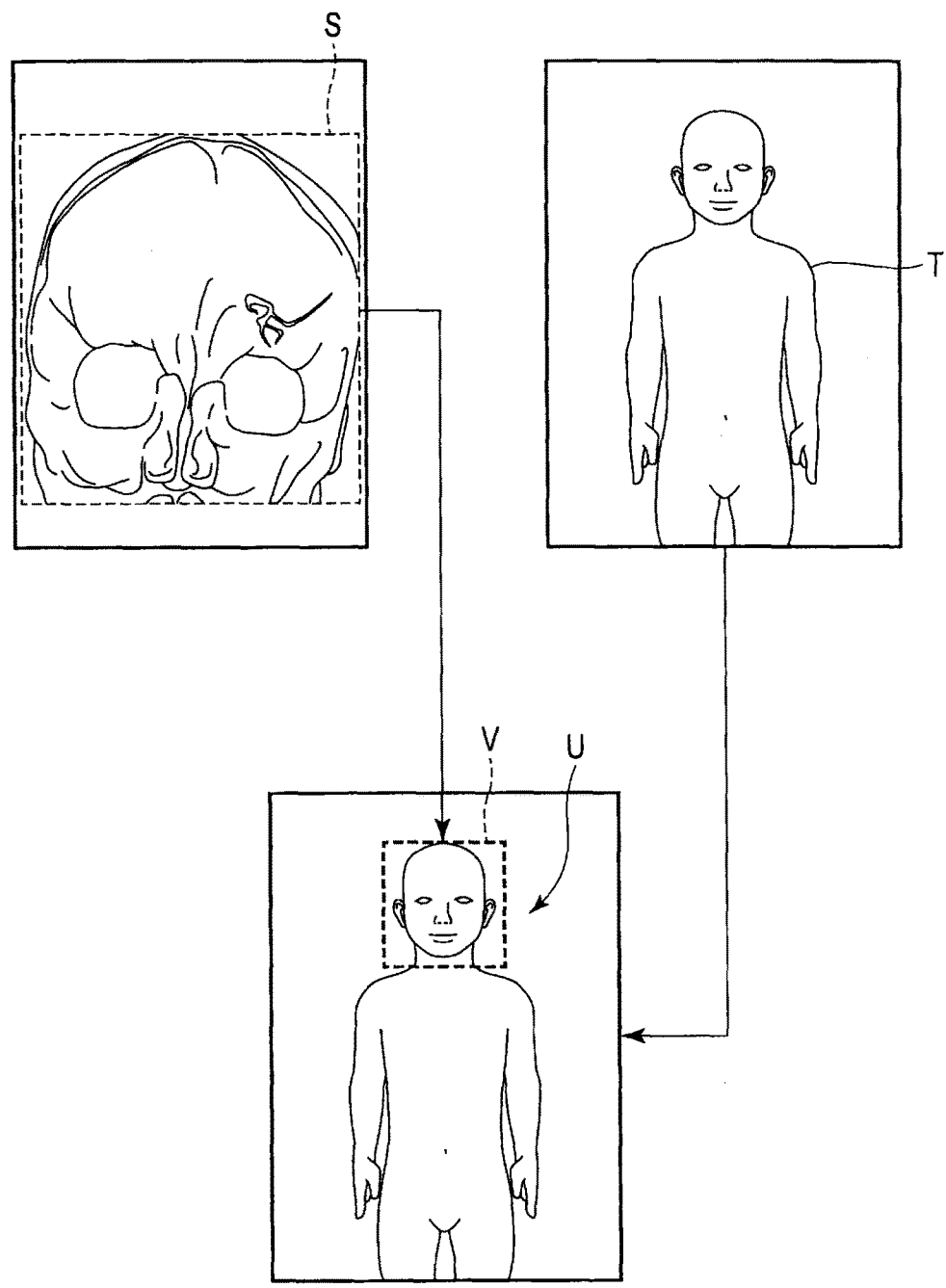
F I G. 11

MEDICAL IMAGE DIAGNOSTIC APPARATUS

FIELD

Embodiments described herein relate generally to a medical image diagnostic apparatus.

BACKGROUND

In diagnosis/medical treatment using an X-ray diagnostic apparatus, a patient is exposed to X-rays. There is available a technique of visualizing the distributions of X-ray incident doses and X-ray exposures to the patient. This technique allows a doctor to perform a surgical operation and X-ray imaging while monitoring an entrance skin dose to the patient. As a consequence, since the doctor can perform a surgical operation in consideration of X-ray exposure to the patient, it is possible to reduce the total incident dose and local incident doses to the patient. In the above technique, the apparatus grasps the position of the X-ray source, the position of the X-ray detector, and the position of the bed, but cannot recognize at which position on the bed a patient is placed. For this reason, it is necessary to estimate or measure the shape and position of the patient.

In the above technique, first of all, the patient is placed on the bed of the X-ray diagnostic apparatus. A model assumed to be most suitable for the patient is then manually selected from a database (or semi-automatically selected by referring to weight information and height information). Many specified models are registered in the database. That is, in the execution of the above technique, it is assumed that the model to be used in the above technique is selected from a plurality of specified models. In addition, the position of the selected model is manually aligned with the position of the X-ray diagnostic apparatus.

However, since the number of models is finite and misselection may occur, the difference in shape between the model and the patient directly leads to a measurement error in an entrance skin dose. In addition, if the actual irradiation range with respect to the patient is shifted from an exposure position on the model by a change in the body shape of the patient, difficulty in accurately grasping the position of the patient on the bed, the movement of the patient during an X-ray examination, and the like, an error occurs in the entrance skin dose.

Under the circumstances, when displaying and calculating an entrance skin dose in the above technique, it is expected to use a shape matching the actual shape of a patient and the position of the patient concerning the X-ray diagnostic apparatus instead of a model. For example, there is available a method of measuring the actual body shape of a patient and specifying the position of the patient concerning the X-ray diagnostic apparatus by using a video camera or installing various types of sensors on the bed.

When, however, using a video camera, a cover such as a drape covering an object sometimes inhibits the patient from being depicted in a video. In this case, it is not possible to grasp the accurate shape of the patient. In addition, even if an infrared camera is used as a video camera, it is only possible to grasp the accurate shape of the patient in one direction by using one camera.

In addition, using sensors imposes certain limitations on the detection of the shape of the patient. Even using, for example, a pressure sensor, a contact sensor, a capacitance sensor, and a temperature sensor as sensors will lead to the occurrence of a positional shift (difference) on a centimeter basis because of factors such as the lifting of part of the patient from the bed.

BRIEF DESCRIPTION OF THE DRAWING

FIG. 2 is a view showing a plurality of object models of males according to the first embodiment;

FIG. 3 is a view showing another object model according to the first embodiment;

FIG. 4 is a view showing still another object model according to the first embodiment:

FIG. 6 is a flowchart showing an example of a processing procedure associated with positional shift correction processing according to the first embodiment;

FIG. 11 is a view showing volume data, an object model, and a partial measurement model according to the fourth modification of the first embodiment;

DETAILED DESCRIPTION

Figure 1:
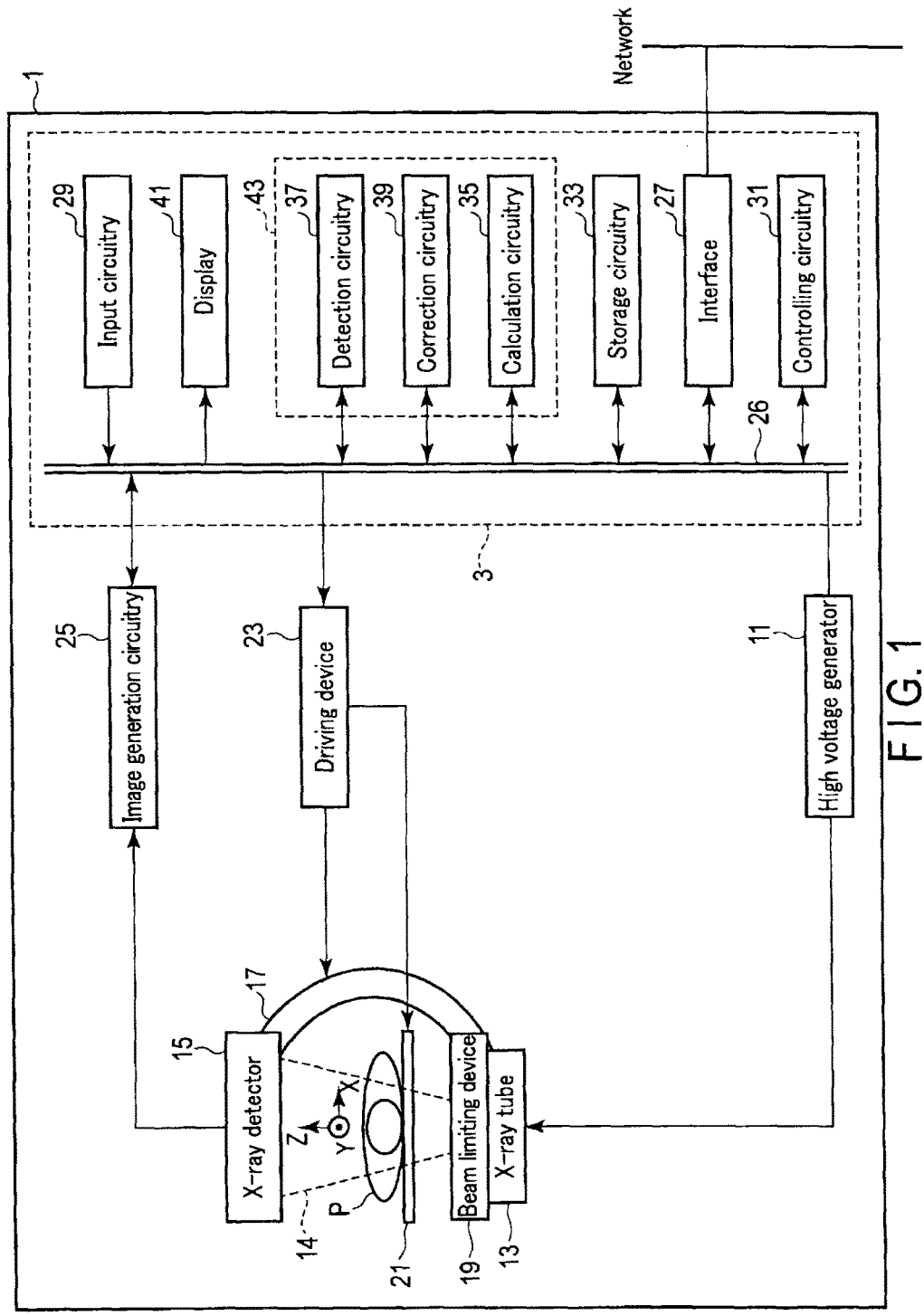
FIG. 1 is a block diagram showing the arrangement of an X-ray diagnostic apparatus according to the first embodiment.

In general, according to one embodiment, a medical image diagnostic apparatus includes an X-ray tube, X-ray detector, image generation circuitry, display, and correction circuitry. The X-ray tube generates X-rays to an object. The X-ray detector detects the X-rays. The image generation circuitry generate an X-ray image based on the detected X-rays. The display displays an incident dose of the X-rays on the object, on an object image indicating the object. The correction circuitry correct a relative positional relationship between the object image and a display area of the incident dose on the object image based on the X-ray image.

First Embodiment

An X-ray diagnostic apparatus will be described below as an example of a medical image diagnostic apparatus according to the first embodiment with reference to the accompanying drawings. Note that the same reference numerals in the following description denote constituent elements having almost the same functions and arrangements, and a repetitive description will be made only when required.

FIG. 1 is a block diagram showing the arrangement of an X-ray diagnostic apparatus 1 according to this embodiment. The X-ray diagnostic apparatus 1 includes a high voltage generator 11, an X-ray tube 13, an X-ray detector 15, a support frame 17, a beam limiting device 19, a bed (not shown) having a patient table 21, a driving device 23 which drives the bed, the patient table 21, and the support frame 17, image generation circuitry 25, a data bus 26, an interface 27, input circuitry 29, controlling circuitry 31, storage circuitry 33, calculation circuitry 35, detection circuitry 37, correction circuitry 39, and a display 41.

The high voltage generator 11 generates tube current to be supplied to the X-ray tube 13 and a tube voltage to be applied to the X-ray tube 13. For example, the high voltage generator 11 includes high voltage generation circuitry which generates a tube current and a tube voltage and a filament current generator which supplies a filament current to the cathode filament of the X-ray tube 13. The high voltage generator 11 supplies tube currents respectively suitable for X-ray imaging and X-ray fluoroscopy to the X-ray tube 13 and applies tube voltages respectively suitable for X-ray imaging and X-ray fluoroscopy to the X-ray tube 13 in accordance with X-ray generation conditions (to be described later) under the control of the controlling circuitry 31.

X-ray generation conditions include, for example, a tube current, a tube voltage, an irradiation time, and the product (to be referred to as the tube current time product (mAs) hereinafter) of a tube current (mA) and an irradiation time (s) at each time of irradiation with X-rays. Note that the high voltage generator 11 may use a scheme of temporally continuously applying a tube voltage to the X-ray tube 13 or a scheme of applying pulse-like high voltages to the X-ray tube 13 by high voltage switching.

The X-ray tube 13 generates X-rays to an object P upon reception of outputs from the high voltage generator 11. More specifically, the X-ray tube 13 generates X-rays at an X-ray focus (to be referred to as a tube focus hereinafter) based on the tube current supplied from the high voltage generator 11 and the tube voltage applied from the high voltage generator 11. The X-ray tube 13 irradiates the object P with the X-rays generated from the tube focus via the X-ray radiation window provided on the front surface of the X-ray tube 13. Referring to FIG. 1, dotted lines 14 indicate an X-ray radiation range. In the following description, assume that the X-ray tube 13 in this embodiment is a rotating anode type X-ray tube. Note that other types of X-ray tubes such as a fixed anode type X-ray tube can also be applied to this embodiment.

The X-ray tube 13 includes a cathode filament and a rotating anode target. The X-ray tube 13 mechanically supports a disk-like anode target by a rotating member and a fixed member which have a bearing between them. The X-ray tube 13 rotates the disk-like anode target by supplying a rotational drive force to the electromagnetic coil of the stator arranged at a position corresponding to the position of the rotating member outside the vacuum tube.

The filament current supplied from the filament current generator of the high voltage generator 11 is supplied to the cathode filament. The cathode filament is heated to a predetermined temperature by the filament current. The heated cathode filament emits electrons. The emitted electrons are caused to collide with the anode target by the tube voltage between the cathode filament and the anode target. X-rays are generated by the electrons which have collided with the anode target.

The X-ray detector 15 detects the X-rays generated from the X-ray tube 13 and transmitted through the object P. For example, the X-ray detector 15 includes a flat panel detector (to be referred to as an FPD hereinafter). The FPD has a plurality of semiconductor detection elements. Each semiconductor detection element includes a direct conversion type and an indirect conversion type. The direct conversion type is a form for directly converting incident X-rays into an electrical signal. The indirect conversion type is a form for converting incident X-rays into light through a phosphor and converting the light into an electrical signal. Note that an image intensifier may be used as the X-ray detector 15.

The electrical signals generated by a plurality of semiconductor detection elements upon incidence of X-rays are output to an analog to digital converter (to be referred to as an A/D converter hereinafter) (not shown). The A/D converter converts the electrical signals into digital data. The A/D converter outputs the digital data to the image generation circuitry 25.

The support frame 17 movably supports the X-ray tube 13 and the X-ray detector 15. More specifically, the support frame 17 is, for example, a C-arm. The C-arm supports the X-ray tube 13 and the X-ray detector 15 so as to make them face each other. A support (not shown) supports the C-arm via, for example, a guide rail and a bearing so as to make the C-arm slidable in a direction (to be referred to as a C direction hereinafter) along the C shape of the C-arm.

In addition, the support supports the C-arm via, for example, a bearing so as to make the C-arm rotatable in a direction (to be referred to as a C orthogonal direction hereinafter) orthogonal to the C direction. Note that the support can also support the C-arm via, for example, a bearing so as to make the C-arm translatable in the short-axis direction (the X direction in FIG. 1) and the long-axis direction (Y direction in FIG. 1) of the patient table 21. In addition, the C-arm supports the X-ray tube 13 and the X-ray detector 15 via, for example, a guide rail and a direct acting bearing so as to make it possible to change the distance (Source Image Distance to be referred to as SID hereinafter) between the tube focus of the X-ray tube 13 and the center of the X-ray detector 15.

Note that the support frame 17 may output the position of the X-ray tube 13 concerning the patient table 21 to the calculation circuitry 35 at the time of X-ray fluoroscopy and X-ray imaging. In this case, the support frame 17 includes a position detector for detecting the position of the X-ray tube 13 concerning the patient table 21.

An Ω-arm may be used as the support frame 17 instead of the C-arm. The X-ray tube 13 and the X-ray detector 15 are mounted on the Ω-arm so as to face each other. A frame which supports the Ω-arm supports the Ω-arm via, for example, a guide rail and a bearing so as to make the Ω-arm slidable in a direction (to be referred to as an Ω direction hereinafter) along the Ω shape of the Ω-arm.

A frame which supports the Ω-arm is installed so as be movable along, for example, the rail installed on the ceiling of an examination room in which the X-ray diagnostic apparatus 1 is installed. The rail is provided, for example, on the ceiling so as to be parallel to the long-axis direction of the patient table 21. The frame supports the Ω-arm via, for example, a bearing so as to make the Ω-arm rotatable in a direction (to be referred to as an Ω orthogonal direction hereinafter) orthogonal to the Ω direction. Note that the frame can also support the Ω-arm via, for example, a bearing so as to make the Ω-arm translatable in the short-axis direction (the X direction in FIG. 1) and the long-axis direction (the Y direction in FIG. 1) of the patient table 21. In addition, the Ω-arm supports the X-ray tube 13 and the X-ray detector 15 via, for example, a guide rail and a direct acting bearing so as to make it possible to change the distance (SID) between the tube focus and the X-ray detector 15.

Note that the support frame 17 in the X-ray diagnostic apparatus 1 according to this embodiment is not limited to the structures using the C-arm and the Ω-arm. The support frame 17 may be supported by, for example, two arms (e.g., robot arms), which independently support the X-ray tube 13 and the X-ray detector 15, via, for example, a bearing, a guide rail, and a direct acting bearing so as to be movable in an arbitrary direction. In addition, the support frame 17 may have a biplane structure constituted by a C-arm and an Ω-arm.

In addition, the support frame 17 in the X-ray diagnostic apparatus 1 according to this embodiment is not limited to an over tube system, an under tube system, and the like and can be applied to an arbitrary form.

The beam limiting device 19 is provided on the front surface of the X-ray radiation window. More specifically, the beam limiting device 19 limits the irradiation field (irradiation range) of X-rays passing through the X-ray radiation window. The beam limiting device 19 is also called an X-ray stop or collimator.

More specifically, in order to prevent a region other than a desired imaging region of the operator from being unnecessarily exposed to the X-rays generated at the tube focus, the beam limiting device 19 limits the irradiation range of the maximum aperture in accordance with the irradiation area of the body surface of the object P which is irradiated with X-rays. For example, the beam limiting device 19 limits the irradiation field by moving the stop blades under the control of the controlling circuitry 31 in accordance with the irradiation field limit instruction input from the input circuitry 29 or a control instruction from the controlling circuitry 31.

The beam limiting device 19 includes a plurality of first stop blades which can move in a predetermined direction and a plurality of second stop blades which can move in a direction different from the predetermined direction. Each of the first and second stop blades is formed from lead which blocks the X-rays generated at the tube focus.

Note that the beam limiting device 19 may include a plurality of predetermined filters (to be referred to as radiation quality adjustment filters hereinafter) to be inserted into the X-ray irradiation field to reduce the incident dose to the object P and improve image quality. The plurality of radiation quality adjustment filters respectively have different thicknesses. Note that the respective radiation quality adjustment filters may be formed from different materials and have the same thickness. Each radiation quality adjustment filter changes the radiation quality of the X-rays generated at the tube focus in accordance with the thickness. Each radiation quality adjustment filter may be formed from aluminum, copper, or the like.

Note that the beam limiting device 19 may output the information of the irradiation field limited by the stop blades and the information of radiation quality adjustment filters at the time of X-ray fluoroscopy and X-ray imaging to the calculation circuitry 35. The information of the limited irradiation field corresponds to the opening degree of the stop, i.e., the aperture area. The opening degree of the stop is specified by, for example, a position detector which detects the position of the stop. In addition, the information of each radiation quality adjustment filter includes the type and thickness of the radiation quality adjustment filter arranged in an irradiation range of the X-ray (X-ray irradiation range).

The bed (not shown) has the patient table 21 (also called a supine table) on which the object P is placed. The object P is placed on the patient table 21. At the time of X-ray fluoroscopy and X-ray imaging, the object P placed on the patient table 21 is arranged between the X-ray tube 13 and the X-ray detector 15. Note that the bed may output the position of the patient table 21 to the calculation circuitry 35 at the time of X-ray fluoroscopy and X-ray imaging. In this case, the bed includes a position detector for specifying the position of the patient table 21.

The driving device 23 drives, for example, the support frame 17, the patient table 21, and the bed. The driving device 23 includes, for example, a motor and a transmission mechanism (e.g., a chain drive, a belt drive, and ball screws) which transmits the force generated by the motor to various types of units as driving targets. The driving device 23 slides the support frame 17 in the C direction and rotates it in the C orthogonal direction in accordance with drive signals corresponding to control signals from the controlling circuitry 31. The driving device 23 may rotate the X-ray detector 15 concerning the X-ray tube 13 under the control of the controlling circuitry 31.

The driving device 23 moves the patient table 21 by driving it under the control of the controlling circuitry 31. More specifically, the driving device 23 slides the patient table 21 in the short-axis direction (the X direction in FIG. 1) of the patient table 21 and the long-axis direction (the Y direction in FIG. 1) of the patient table 21 via, for example, a bearing, a guide rail, and a direct acting bearing based on a control signal from the controlling circuitry 31. In addition, the driving device 23 vertically moves the patient table 21 in the vertical direction (the Z direction in FIG. 1) via, for example, a bearing, a guide rail, and a direct acting bearing.

In addition, the driving device 23 may rotate the patient table 21 to tilt it, with at least one of the long-axis direction and the short-axis direction being a rotation axis (the X- and Y-axes in FIG. 1), via, for example, a bearing, a guide rail, and a direct acting bearing. The driving device 23 outputs the position of the X-ray tube 13 concerning the patient table 21 and the position of the patient table 21 to the calculation circuitry 35 at the time of X-ray fluoroscopy and X-ray imaging.

The image generation circuitry 25 generates an X-ray image based on the X-rays detected by the X-ray detector 15. More specifically, the image generation circuitry 25 is a processor which generates an X-ray image by preprocessing the data output from the X-ray detector 15. For example, the image generation circuitry 25 reads out a program corresponding to the preprocessing function (to be referred to as a preprocessing program hereinafter) from the storage circuitry 33 and executes the readout preprocessing program, thereby implementing the preprocessing function.

The preprocessing function is a function of executing preprocessing for the digital data output from the X-ray detector 15. Preprocessing includes correction of sensitivity unevenness between the channels in the X-ray detector 15 and correction concerning an excessive decrease in signal level or data dropout caused by an X-ray absorber such as a metal.

In addition, the image generation circuitry 25 reads out a program corresponding to an image generation function (to be referred to as an image generation program hereinafter)

from the storage circuitry 33, and executes the readout image generation program, thereby implementing the image generation function. The image generation circuitry 25 is connected to, for example, the data bus 26 in FIG. 1.

The image generation function includes a function of generating an obtained image based on the digital data preprocessed after X-ray imaging at an imaging position and a function of generating a fluoroscopic image based on the digital data preprocessed after X-ray fluoroscopy at a fluoroscopy position. Obtained images and fluoroscopic images will be collectively referred to as X-ray images hereinafter. The image generation circuitry 25 sequentially generates fluoroscopic images in real time. The image generation function outputs a generated X-ray image to, for example, the storage circuitry 33, the detection circuitry 37, the correction circuitry 39, the display 41, and the like.

The image generation circuitry 25 generates a superimposed image (to be referred to as a dose image hereinafter) obtained by superimposing an incident dose on an object image (object model) (to be described later) in accordance with irradiation of the object P with X-rays in response to an instruction to start a dose display function (to be described later). An incident dose is, for example, an entrance skin dose on an object body surface. The image generation circuitry 25 sequentially outputs generated dose images to the display 41. Note that the image generation circuitry 25 may output, to the storage circuitry 33, the dose images generated in chronological order in an X-ray examination on the object P.

The image generation circuitry 25 is a processor which includes processing circuitry, reads out various types of programs from, for example, the storage circuitry 33, and executes the programs, thereby implementing functions corresponding to the readout programs. In other words, the processing circuitry which has read out programs has the preprocessing function and the image generation function.

According to the above description, the single processing circuitry executes various functions such as the preprocessing function and the image generation function. However, a plurality of independent processors may be combined to form processing circuitry, and the respective processors execute programs to implement the respective types of functions. Alternatively, the preprocessing function and the image generation function may be implemented by different processing circuits.

The word "processor" used in the above description means circuitry such as a CPU (Central Processing Unit), a GPU (Graphics Processing Unit), an ASIC (Application Specific Integrated Circuit), a programmable logic device (e.g., an SPLD (Simple Programmable Logic Device), a CPLD (Complex Programmable Logic Device), or an FPGA (Field Programmable Gate Array)), or the like.

Note that it is possible to directly incorporate programs in the circuitry of the processor instead of storing them in the storage circuitry 33. In this case, the processor implements various types of functions by reading out programs incorporated in the circuitry and executing them.

Note that each processor in this embodiment may be formed as one processor by combining a plurality of independent circuits to implement various types of functions as well as being formed as single circuitry for each processor. In addition, a plurality of constituent elements in FIG. 1 may be integrated into one processor to implement the corresponding function.

The interface 27 is an interface associated with, for example, a network and an external storage device (not shown). Data such as the X-ray images obtained by the X-ray diagnostic apparatus 1, analysis results, and the like can be transferred to other apparatuses via the interface 27 and the network. The interface 27 connects the X-ray diagnostic apparatus 1 to an electronic communication line (to be referred to as a network hereinafter). Various types of modalities (not shown) are connected to the network, including, for example, a radiology department information management system, a hospital information system, an X-ray computed tomography apparatus (to be referred to as an X-ray CT apparatus hereinafter), and a magnetic resonance imaging apparatus (to be referred to as an MRI apparatus hereinafter).

The input circuitry 29 inputs, to the X-ray diagnostic apparatus 1, various types of instructions, commands, information, selections, and settings from the operator. For example, the input circuitry 29 inputs X-ray generation conditions such as imaging conditions for X-ray imaging and fluoroscopy conditions for X-ray fluoroscopy, X-ray irradiation ranges associated with fluoroscopy and imaging positions, an ROI (Region of Interest) on an X-ray image, and the like, which are desired by the operator, in accordance with instructions from the operator. X-ray generation conditions include, for example, a tube voltage, a tube current, an irradiation time, irradiation field information, and radiation quality adjustment filter information.

The input circuitry 29 is implemented by a trackball, switch buttons, a mouse, a keyboard, and the like which are used to set and input various types of settings such as a region of interest, a radiation quality adjustment filter, and X-ray generation conditions. The input circuitry 29 outputs the various instructions input by the operator to various types of circuits such as the controlling circuitry 31. The input circuitry 29 detects the coordinates of the cursor displayed on the display 41, and outputs the detected coordinates to the controlling circuitry 31.

Note that the input circuitry 29 may be a touch panel provided to cover the display 41. In this case, the input circuitry 29 detects touched and designated coordinates by a coordinate reading principle such as an electromagnetic induction scheme, magnetostriction scheme, or a pressure-sensitive scheme, and outputs the detected coordinates to the controlling circuitry 31.

The input circuitry 29 has buttons, switches, and the like associated with the start, end, and stop of X-ray imaging and X-ray fluoroscopy. In addition, the input circuitry 29 has a button, switch, or the like for inputting an instruction to start a function (to be referred to as a dose display function hereinafter) of displaying the distribution of entrance skin doses on the object P at the time of X-ray imaging and X-ray fluoroscopy with respect to the object P.

The input circuitry 29 inputs an instruction to select an object image on which entrance skin doses are superimposed at the time of the startup of the dose display function. An object image is an image indicating the object P, and is, for example, a three-dimensional image schematically indicating the object P. A three-dimensional image schematically indicating the object P is, for example, an object model three-dimensionally indicating the object P. An object model is, for example, a schematic rendering image (surface rendering image or a volume rendering image).

The input circuitry 29 may also be implemented by a footswitch provided near the bed. The footswitch inputs an instruction to start, end, or stop X-ray imaging and X-ray fluoroscopy in accordance with an instruction from the operator. The input circuitry 29 may input the positional shift (difference) between an X-ray irradiation range and the display area of entrance skin doses on an object model.

The controlling circuitry 31 is a processor which controls the respective units, the respective processing circuits, the driving device, and the like in the X-ray diagnostic apparatus 1. The controlling circuitry 31 includes a CPU and a memory (neither shown). The controlling circuitry 31 reads out programs (to be referred to as system control programs hereinafter) for controlling the respective units, the respective processing circuits, the driving device, and the like in the X-ray diagnostic apparatus 1 from the storage circuitry 33, and execute the readout system control programs, thereby implementing various types of control functions.

The control function temporarily stores, in a memory (not shown), the operator's instructions, the information of X-ray generation conditions such as imaging conditions and fluoroscopy conditions, the irradiation field information, the radiation quality adjustment filter information, and the like which are sent from the input circuitry 29. The controlling circuitry 31 controls the high voltage generator 11, the X-ray detector 15, the beam limiting device 19, the bed, the patient table 21, the driving device 23, and the like to execute X-ray imaging/X-ray fluoroscopy (pulse X-ray imaging) in accordance with the above pieces of information stored in the memory.

According to the above description, the single controlling circuitry executes various functions such as the controlling function. However, a plurality of independent processors may be combined to form a controlling circuitry, and the respective processors execute programs to implement the respective types of functions.

In addition, each processor (the image generation circuitry 25 and the controlling circuitry 31) in this embodiment may be formed as one processor by combining a plurality of independent circuits to implement the respective types of functions as well as being formed as single circuitry for each processor. In addition, the image generation circuitry 25 and the controlling circuitry 31 may be integrated into one processor to implement the corresponding function.

The word "processor" used in the above description means circuitry such as a CPU, GPU, ASIC, SPLD, CPLD, or FPGA. The processor implements various types of functions by reading out programs stored in the storage circuitry 33 and executing them. Note that it is possible to directly incorporate programs in the circuitry of the processor in the controlling circuitry 31 instead of storing them in the storage circuitry 33. In this case, the processor implements various types of functions by reading out system control programs incorporated in the circuitry and executing them.

The storage circuitry 33 includes various types of memories, an HDD (Hard Disk Drive), an SSD (Solid State a Drive), a magnetic disk (a Floppy® disk, hard disk, or the like), an optical disk (a CD-ROM, DVD, or the like), and a semiconductor memory.

The storage circuitry 33 stores a diagnosis protocol, the operator's instructions sent from the input circuitry 29, various types of data groups concerning X-ray generation conditions such as imaging conditions concerning X-ray imaging and fluoroscopy conditions, irradiation field information at the time of irradiation of an object with X-rays, radiation quality adjustment filter information, and the like.

The storage circuitry 33 stores various types of X-ray images generated by the image generation circuitry 25, a plurality of object images, and the like. The plurality of object images are object models corresponding to the sex, age, weight, height, and the like of patients. That is, the plurality of object models are models corresponding to pieces of information indicating the sex, adult/child, exceeding standard weight, standard weight, less than standard weight, weight range, height range, X-ray irradiation region, and the like. An object image will be referred to as an object model hereinafter.

FIG. 2 is a view showing an example of a plurality of object models of males. The uppermost row in FIG. 2 shows object models exceeding standard weight, showing five object models in descending order of height. The intermediate row in FIG. 2 shows object models corresponding to the standard weight, showing five object models in descending order of height. The lowermost row in FIG. 2 shows object models less than the standard weight, showing five object models in descending order of height.

Reference symbols S1 and S2 in FIG. 3 each denote an example of an object model. Reference symbol IR in FIG. 3 denotes an X-ray irradiation range. Reference symbol DS1 in FIG. 3 denotes the display area of entrance skin doses on the object model S1. Reference symbol DS2 in FIG. 3 denotes the display area of entrance skin doses and entrance skin doses on the object model S2.

Note that the display area of entrance skin doses on an object model may have, for example, a cylindrical shape as indicated by "Cy" in FIG. 4. In addition, an object model is not limited to a cylindrical shape and may have an arbitrary stereoscopic shape (e.g., a cubic shape, rectangular parallelepiped shape, or polyhedral shape). Reference symbol S3 in FIG. 4 denotes an object model. When an object model has a cylindrical shape, the storage circuitry 33 stores an X-ray detector model Xd, an X-ray tube model Xt, and an irradiation range Xir, as shown in FIG. 4. The size of an irradiation range is determined by the calculation circuitry 35. Reference symbol DS3 in FIG. 4 denotes the distribution of entrance skin doses displayed on the object model.

In addition, the storage circuitry 33 may store shape models corresponding to imaging regions as object models. A shape model corresponding to an imaging region is, for example, a spherical model when the imaging region is the head region. In addition, a shape model corresponding to an imaging region is a cylindrical model when the imaging region is the abdominal region.

Figure 5:
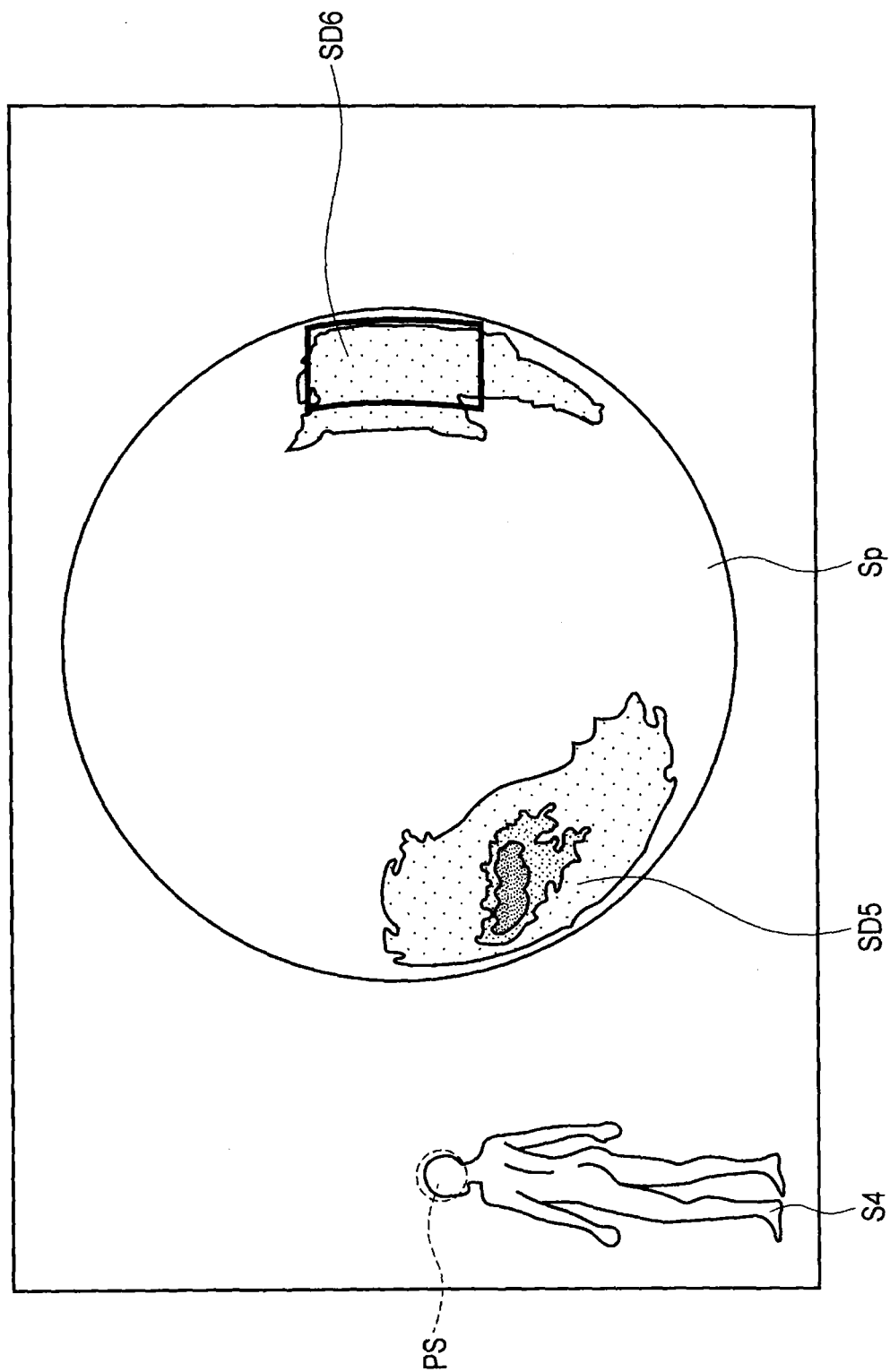
FIG. 5 is a view showing still another object model according to the first embodiment.

FIG. 5 shows an example of a shape model when the imaging region is the head region. Reference symbol Sp in FIG. 5 denotes a spherical model. Reference symbols SD5 and SD6 in FIG. 5 each denote the distribution of entrance skin doses displayed on the spherical model. Reference symbol S4 in FIG. 5 denotes an object model for indicating a region of the shape model. Reference symbol PS in FIG. 5 denotes the position of the spherical model Sp of the object model S4.

The storage circuitry 33 stores a plurality of anatomical landmarks of a plurality of object models. Anatomical landmarks include, for example, edges, eyes, and bones. That is, each object model has a plurality of anatomical landmarks.

The storage circuitry 33 may store, for each object model, patterns and markers indicating anatomical structures (anatomical features) concerning predetermined organs instead of anatomical landmarks. Predetermined organs are, for example, organs highly sensitive to X-rays (i.e., regions for which careful consideration is given to exposure), and include, for example, the crystalline lens and the thyroid gland. Patterns and markers indicating anatomical structures will be referred to as anatomical regions hereinafter.

The storage circuitry 33 stores the entrance skin doses calculated over a period of an X-ray examination executed for the object P and the display area of entrance skin doses on the object model in correspondence with the X-ray irradiation times. That is, the storage circuitry 33 stores the entrance skin doses along the time series and the display area of the entrance skin doses.

The storage circuitry 33 stores various types of programs including system control programs for the X-ray diagnostic apparatus 1, a preprocessing program concerning the preprocessing function, an image generation program concerning the image generation function, a dose calculation program for calculating entrance skin doses, a positional shift detection program for detecting the positional shift between an X-ray irradiation range and the display area of entrance skin doses on an object model, a correction program for correcting the relative positional relationship between an object image and the display area of entrance skin doses, and a registration program for executing registration between an X-ray image and the image obtained by superimposing entrance skin doses on an object model.

The storage circuitry 33 stores predetermined thresholds (a positional shift angle range and a positional shift length range) used by the positional shift detection program, the relative positional relationship corrected by the correction circuitry 39, and the like. A predetermined threshold is a value as a trigger for positional shift detection, and set on the millimeter (mm) order. Note that a predetermined threshold may be dependent on the size of a predetermined organ (e.g., the size (diameter) of the eye) displayed on an X-ray image.

Based on X-ray generation conditions, the position of the X-ray tube 13, the position of the patient table 21, and a selected object model, the calculation circuitry 35 calculates the irradiation position of X-rays on the object model and an X-ray dose at each time of irradiation of the object with X-rays. More specifically, the calculation circuitry 35 calculates an entrance skin dose by integrating X-ray doses at each irradiation position and each time of irradiation with X-rays. In addition, the calculation circuitry 35 calculates the display area of entrance skin doses on the object model by adding irradiation positions at each time of irradiation with X-rays except for each region where irradiation positions overlap.

The calculation circuitry 35 outputs the display area of entrance skin doses and the entrance skin dose calculated at each time of irradiation with X-rays to the display 41. The calculation circuitry 35 also outputs the display area of the entrance skin doses and the entrance skin doses to the storage circuitry 33 in correspondence with X-ray irradiation times. The calculation circuitry 35 outputs the display area of the entrance skin doses to the detection circuitry 37 at each time of irradiation with X-rays.

The calculation circuitry 35 is a processor which has processing circuitry and reads out and executes a dose calculation program from the storage circuitry 33, thereby implementing a function corresponding to the readout program. According to the above description, the single processing circuitry executes the function of calculating entrance skin doses and the display area of the entrance skin doses on an object model. However, a plurality of independent processors may be combined to form processing circuitry, and each processor may execute a dose calculation program to implement a corresponding function.

The word "processor" used in the above description means circuitry such as a CPU, GPU, ASIC, SPLD, CPLD, or FPGA. Note that it is possible to directly incorporate programs in the circuitry of the processor instead of storing them in the storage circuitry 33. In this case, the processor implements various types of functions by reading out programs incorporated in the circuitry and executing them.

Note that each processor (the controlling circuitry 31 and the calculation circuitry 35) in this embodiment may be formed as one processor by combining a plurality of independent circuits to implement various types of functions as well as being formed as single circuitry for each processor.

The detection circuitry 37 detects the positional shift (positional shift or size difference) between the display area of entrance skin doses (X-ray irradiation range) on an object model and an X-ray image (an X-ray irradiation range on the X-ray image). More specifically, the detection circuitry 37 executes registration between an edge of the object on an X-ray image and an edge of an object model. Note that the detection circuitry 37 may execute registration between a bone region of an object on an X-ray image and a bone region of an object model.

In addition, the detection circuitry 37 may execute registration between the position of the eye (the position of the crystalline lens) on an X-ray image and the position of the eye on an object model. The detection circuitry 37 detects an edge, a bone region, the position of the eye, and the like (anatomical features) in advance by, for example, performing edge detection or using an atlas (anatomical diagram) or the like. The registration used by the detection circuitry 37 is, for example, rigid registration. Note that the registration to be used is not limited to rigid registration.

Note that if an object model is provided with anatomical landmarks or anatomical regions, the detection circuitry 37 detects anatomical landmarks or anatomical regions on an X-ray image. The detection circuitry 37 then executes registration between the X-ray image and the object model by using the corresponding anatomical landmarks or the corresponding anatomical regions (the position of the eye, the position of the crystalline lens, and the like) on the X-ray image and the object model. Note that registration may be executed in a composite manner using edges, anatomical features, anatomical landmarks, and the like.

The detection circuitry 37 detects the positional shift between an X-ray irradiation range and the display area of entrance skin doses on the object model by using the registered X-ray image and object model and a predetermined threshold. If, for example, the magnitude of the positional shift exceeds a predetermined threshold, the detection circuitry 37 detects the positional shift. Note that the detection circuitry 37 may detect the positional shift of a predetermined organ, i.e., an organ highly sensitive to X-rays. In addition, the detection circuitry 37 detects the difference in size (i.e., the size difference) between an X-ray irradiation range and the display area of entrance skin doses based on the registered X-ray image and object model. Note that the detection circuitry 37 may detect the difference in accordance with an instruction from the operator via the input circuitry 29.

Upon detecting the positional shift, the detection circuitry 37 outputs the positional shift amount (the magnitude (length) of the positional shift and the direction of the shift) to the correction circuitry 39. Note that the detection circuitry 37 may output the positional shift amount and information concerning the positional shift amount to the display 41. In addition, the detection circuitry 37 detects the presence/absence of a positional shift every time an X-ray image is generated.

Information concerning a positional shift amount includes, for example, a message for moving an object model or the display area of entrance skin doses, an arrow indicating a direction in which an object model or the display area of entrance skin doses is moved, a support message indicating in which direction and how much an object model or the display area of entrance skin doses should be moved, information presenting a more suitable object model in accordance with the magnitude of the positional shift amount (enlargement/reduction (resizing)), and a predetermined warning for notifying the occurrence of the positional shift.

The detection circuitry 37 is a processor which has processing circuitry and reads out and executes various types of programs (the positional shift detection program, the registration program, and the like) from the storage circuitry 33, thereby implementing functions corresponding to the readout programs. According to the above description, the single processing circuitry executes the positional shift detection function. However, a plurality of independent processors may be combined to form processing circuitry, and the respective processors may execute programs to implement the respective types of functions.

The word "processor" used in the above description means circuitry such as a CPU, GPU, ASIC, SPLD, CPLD, or FPGA. Note that it is possible to directly incorporate programs in the circuitry of the processor instead of storing them in the storage circuitry 33. In this case, the processor implements various types of functions by reading out programs incorporated in the circuitry and executing them.

Note that each processor (the calculation circuitry 35 and the detection circuitry 37) in this embodiment may be formed as one processor by combining a plurality of independent circuits to implement various types of functions as well as being formed as single circuitry for each processor. In addition, a plurality of constituent elements in FIG. 1 may be integrated into one processor to implement the corresponding function.

The correction circuitry 39 corrects the relative positional relationship between the display area of entrance skin doses on an object model and an object image based on an X-ray image. For example, the correction circuitry 39 corrects the above relative positional relationship based on anatomical landmarks on an X-ray image and anatomical landmarks on an object model.

More specifically, the correction circuitry 39 corrects at least one of the position of an object model and the size of the object model to match the display area of entrance skin doses on the object model with an X-ray irradiation range based on anatomical landmarks on the X-ray image and an X-ray irradiation range on the body surface of the object. Note that the correction circuitry 39 may correct at least one of the position of the display area of entrance skin doses and the size of the display area of the entrance skin doses on the object model to match the display area of the entrance skin doses on the object model with an X-ray irradiation range based on anatomical landmarks on the X-ray image and the X-ray irradiation range on the body surface of the object.

Note that if the display area of entrance skin doses on an object model can be matched with an X-ray irradiation range based on the relative enlargement ratio or reduction ratio between the respective ranges, the correction circuitry 39 corrects at least one of the object model and the display area of the entrance skin doses by using at least one the relative enlargement ratio and the relative reduction ratio. Alternatively, the correction circuitry 39 may correct at least one of the position of the object model and the size of the object model by rotating the object model based on the positional shift amount. Note that the correction circuitry 39 may perform correction with respect to an object model and the display area of entrance skin doses by combining the above various correction methods.

That is, based on the positional shift amount detected by the detection circuitry 37, the correction circuitry 39 moves or deforms the object model or the display area of the entrance skin doses so as to minimize the positional shift amount. In addition, based on the positional shift amount detected by the detection circuitry 37, the correction circuitry 39 changes (deforms or resizes) the size of the object model or the size of the display area of the entrance skin doses so as to minimize the positional shift amount. In this case, the correction circuitry 39 may select a more suitable object model in accordance with the size (enlargement/reduction) of the positional shift amount.

The correction circuitry 39 is a processor which has processing circuitry and reads out and executes a correction program from the storage circuitry 33, thereby implementing a function corresponding to the readout program. According to the above description, the single processing circuitry executes the positional shift detection function. However, a plurality of independent processors may be combined to form processing circuitry, and the respective processors may execute programs to implement the respective types of functions.

The word "processor" used in the above description means circuitry such as a CPU, GPU, ASIC, SPLD, CPLD, or FPGA. Note that it is possible to directly incorporate programs in the circuitry of the processor instead of storing them in the storage circuitry 33. In this case, the processor implements various types of functions by reading out programs incorporated in the circuitry and executing them.

Note that each processor (the calculation circuitry 35, the detection circuitry 37, and the correction circuitry 39) in this embodiment may be formed as one processor by combining a plurality of independent circuits to implement various types of functions as well as being formed as single circuitry for each processor. In addition, a plurality of constituent elements in FIG. 1 may be integrated into one processor (a processing device 43 in FIG. 1) to implement the corresponding function.

The display 41 displays the X-ray image generated by the image generation circuitry 25 and various types of input items (X-ray generation conditions, an X-ray irradiation range concerning a fluoroscopy/imaging position, a region of interest on an X-ray image, and the like) to be input by the input circuitry 29. The display 41 displays the entrance skin doses originating from X-rays on an object image (object model) indicating the object in response to an instruction to start the dose display function. More specifically, the display 41 displays entrance skin doses on an object model in predetermined hues corresponding to the magnitudes of doses.

More specifically, the display 41 updates and displays entrance skin doses in accordance with irradiation of the object P with X-rays. In this case, the display 41 corrects and displays the relative positional relationship between the object model and the display area of the entrance skin doses in accordance with the correction result obtained by the correction circuitry 39. That is, the display 41 displays a dose image upon correcting at least one of the position of the object model, the size of the object model, the position of the display area of the entrance skin doses on the object model, and the size of the display area of the entrance skin doses on the object model.

Note that the display 41 may rotate and display the object model in accordance with a positional shift amount. In addition, the display 41 may display the object model displayed on a dose image in place of the object model selected in accordance with the magnitude (enlargement/ reduction) of a positional shift amount. This matches, on a dose image, the display area of the entrance skin doses on the object model with the X-ray irradiation range.

The display 41 may display a positional shift amount and information concerning the positional shift amount in response to the detection of the positional shift by the detection circuitry 37. For example, the display 41 displays, for example, a message for moving an object model or the display area of entrance skin doses, an arrow indicating a direction in which an object model or the display area of entrance skin doses is moved, a support message indicating in which direction and how much an object model or the display area of entrance skin doses should be moved, information presenting a more suitable object model in accordance with the magnitude of the positional shift amount (enlargement/reduction), and a predetermined warning for notifying the occurrence of a positional shift.

(Positional Shift Correction Function)

The positional shift correction function is a function of detecting the positional shift between an X-ray irradiation range and the display area of entrance skin doses on an object model and correcting the detected positional shift on a dose image. Processing associated with the positional shift correction function (to be referred to as positional shift correction processing hereinafter) will be described below.

FIG. 6 is a flowchart showing an example of a processing procedure associated with the positional shift correction processing.

The dose display function is activated in response to an instruction from the operator via the input circuitry 29 (step Sa1). At this time, an object model on which entrance skin doses are to be superimposed is selected via the input circuitry 29. Note that an object model to be used by the dose display function may be selected from a plurality of object models by the processing device 43 or the controlling circuitry 31 based on object information (sex, weight, height, and the like) acquired via a network.

Before X-ray imaging, X-ray generation conditions and the like are input to the controlling circuitry 31 in accordance with an instruction from the operator via the input circuitry 29. X-ray imaging is started with respect to an object in accordance with an instruction from the operator via the input circuitry 29 (step Sa2). The object is irradiated with X-rays under the X-ray generation conditions (step Sa3). An X-ray image is generated and displayed on the display 41. The calculation circuitry 35 calculates entrance skin doses and the display area of the entrance skin doses.

The entrance skin doses are superimposed on the display area of the entrance skin doses on an object model and displayed in hues corresponding to the doses on the display 41 (step Sa4). The positional shift between the X-ray image (X-ray irradiation range) and the display area of the entrance skin doses corresponding to irradiation with X-rays (the X-ray irradiation range on the object model which corresponds irradiation with X-rays) is detected (step Sa5). The relative positional relationship between the object model and the display area of the entrance skin doses is corrected (step Sa6). In addition, a positional shift amount and information concerning the positional shift amount may be displayed on the display 41 in accordance with the detection of the positional shift.

Correcting the relative positional relationship corresponds to moving the object model or the X-ray irradiation range on the object model (the display area of the entrance skin doses corresponding to irradiation with X-rays) or changing (deforming) (enlarging/reducing) the size of the object model or the size of the X-ray irradiation range on the object model (the display area of the entrance skin doses corresponding to irradiation with X-rays) on the dose image displayed on the display 41.

Note that correcting the relative positional relationship may correspond to replacing the object model displayed on the dose image with a more suitable object model corresponding to the magnitude (enlargement/reduction) of a positional shift amount. In addition, correcting the relative positional relationship may correspond to rotating the object model displayed on the dose image in accordance with a positional shift amount.

Entrance skin doses are displayed on the object model by using the corrected relative positional relationship (step Sa7). The processing in steps Sa3 to Sa8 is repeated until an instruction to end the X-ray imaging is input via the input circuitry 29 (step Sa8).

Figure 7:
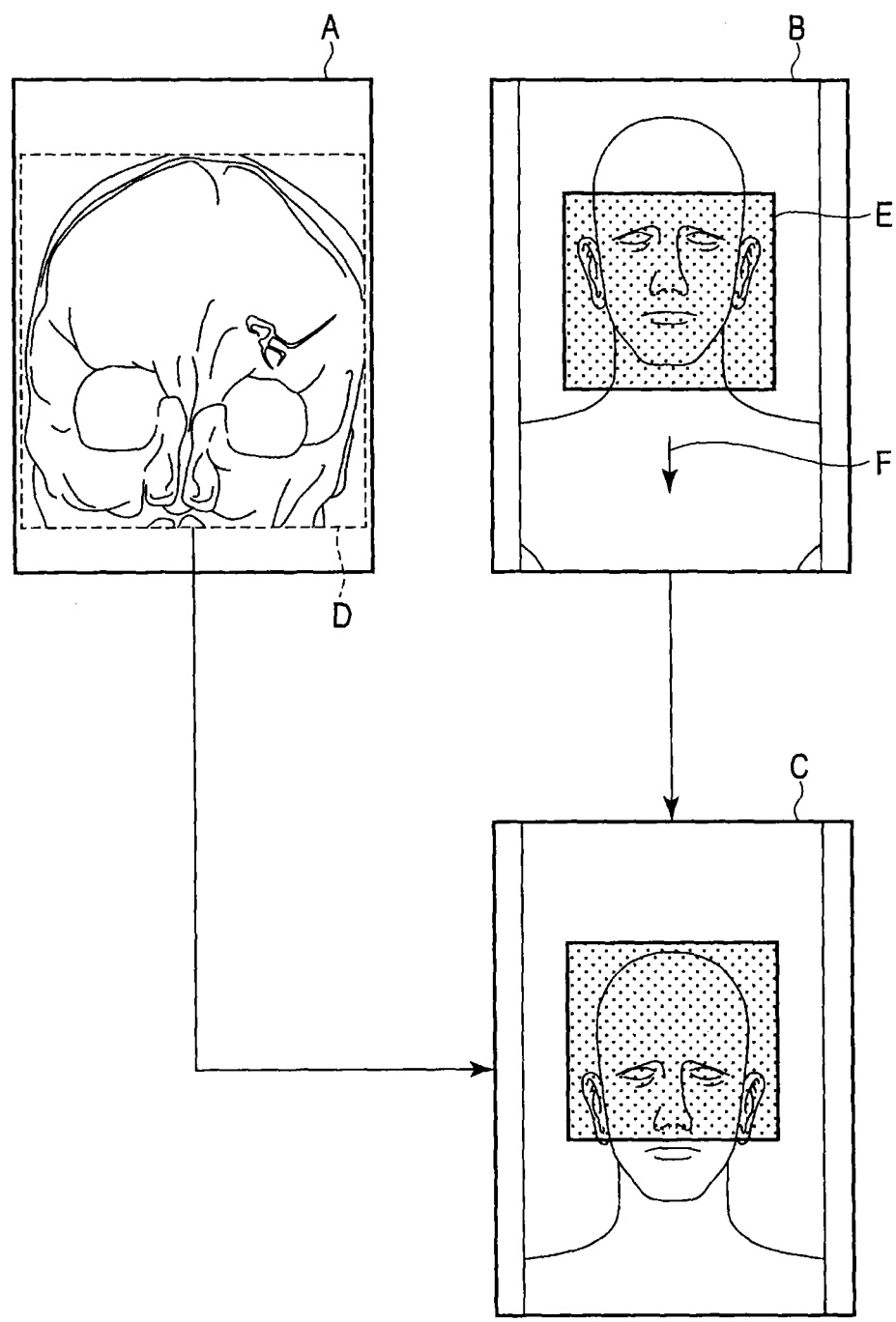
FIG. 7 is a view showing an X-ray image and a dose image which are generated accompanying irradiation of an object with X-rays, and a dose image obtained by moving an object model using a corrected relative positional relationship according to the first embodiment.

FIG. 7 is a view showing an X-ray image A and a dose image B generated accompanying irradiation of the object P with X-rays and a dose image C obtained by moving the object model using a corrected relative positional relationship. As shown in FIG. 7, an X-ray irradiation range D on the object P on the X-ray image A is the range from the crown to the nasal cavity and the maxilla, which differs from a display area E of entrance skin doses (corresponding to irradiation with X-rays) on the dose image B before correction.

As shown in FIG. 7, the detection circuitry 37 detects the positional shift between the X-ray irradiation range D and the display area E of the entrance skin doses. The object model on the dose image C in FIG. 7 has been moved downward (F in FIG. 7) in accordance with the detected positional shift amount.

Figure 8:
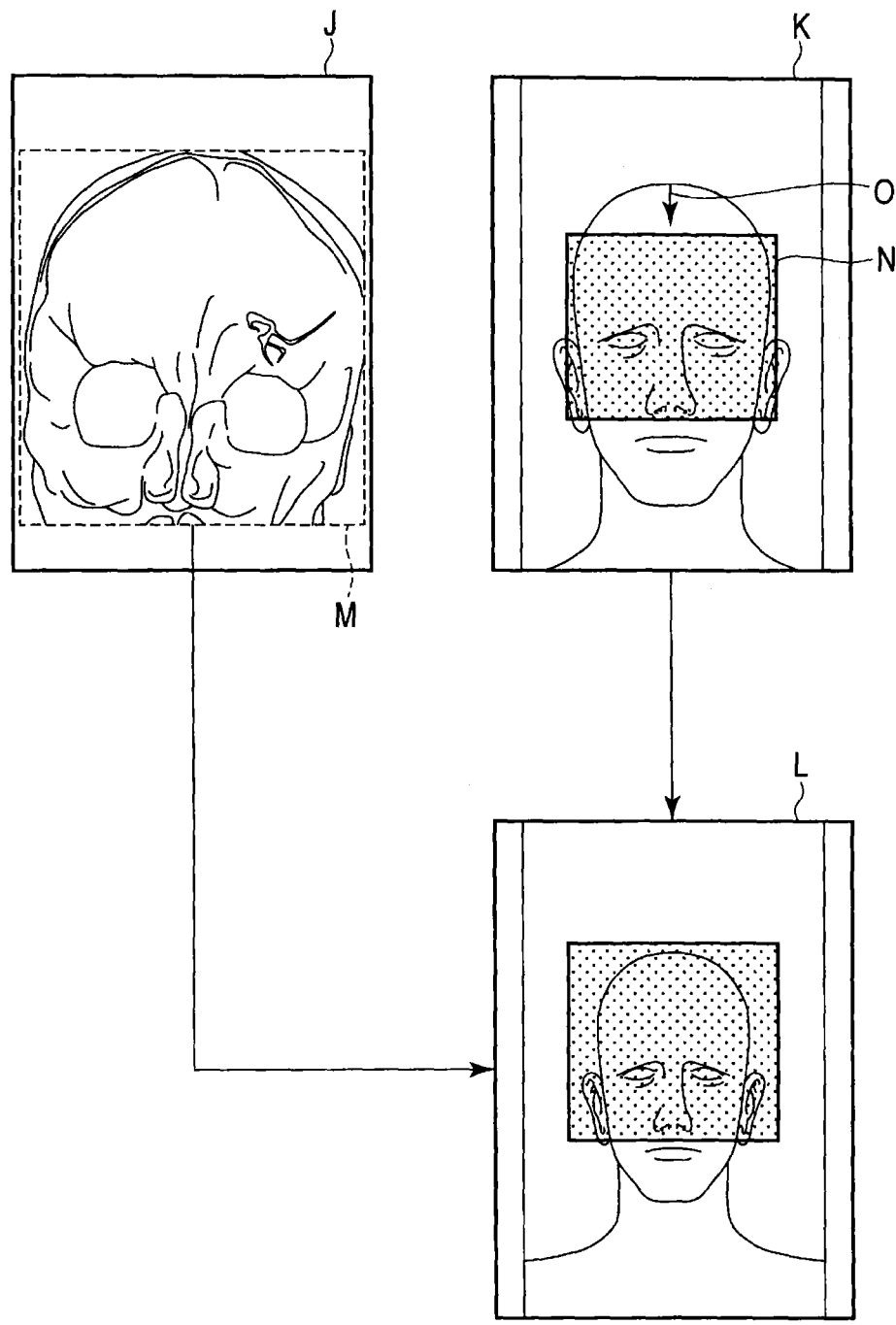
FIG. 8 is a view showing an X-ray image and a dose image which are generated accompanying irradiation of an object with X-rays, and a dose image obtained by moving an object model using a corrected relative positional relationship according to the first embodiment.

FIG. 8 is a view showing an X-ray image J and a dose image K generated accompanying irradiation of the object P with X-rays and a dose image L obtained by moving the object model using a corrected relative positional relationship. An X-ray irradiation range M on the X-ray image J in FIG. 8 is the range from the crown to the nasal cavity and the maxilla, which differs from a display area N of entrance skin doses on the dose image K.

As shown in FIG. 8, the detection circuitry 37 detects the positional shift between the X-ray irradiation range M and the display area N of the entrance skin doses. The positional shift between the X-ray irradiation range M and the display area N originates from the size of the head region of the object model. For this reason, the object model on the dose image C in FIG. 8 has a portion (head region) of the object model reduced (0 in FIG. 8) in accordance with the detected positional shift amount along the body axis direction of the object model. If, for example, the object is a child, the object model may be extended as needed in accordance with the growth of the object (e.g., the age).

According to the above arrangement, the following effects can be obtained.

The X-ray diagnostic apparatus 1 according to this embodiment can correct the relative positional relationship between an object model (object image) and the display arrangement of entrance skin doses concerning irradiation with X-rays on the object model based on an X-ray image at each time irradiation of the object P with X-rays. This makes it possible to improve the accuracy of the shape of an object model concerning the object P and the accuracy of the display area of entrance skin doses without any cumbersome operation by the operator even if the object P has moved (the object has shaken his/her head or has moved his/her feet) during X-ray imaging (for example, in a case in which the object P could not be anesthetized in a long surgical operation). As described above, the X-ray diagnostic apparatus 1 according to the embodiment can improve the problem of the occurrence of an error in the calculation of entrance skin doses.

(First Modification)

A difference from the first embodiment is that positional shift correction processing is executed by using a plurality of X-ray images obtained in different imaging directions.

The input circuitry 29 inputs an instruction to change an imaging direction in accordance with an instruction from the operator during the execution of an X-ray examination on the object P. That is, the input circuitry 29 inputs an instruction to move the support frame 17 in an imaging direction (to be referred to as a different imaging direction hereinafter) different from the imaging direction concerning the above X-ray image. The input circuitry 29 inputs an instruction (to be referred to as an imaging instruction hereinafter) to image the object P from the different imaging direction. Note that the input circuitry 29 may input X-ray generation conditions concerning X-ray imaging in the different imaging direction. The input circuitry 29 outputs the X-ray generation conditions and the different imaging direction to the controlling circuitry 31 and the calculation circuit 35.

The controlling circuitry 31 outputs, to the driving device 23, an instruction to move the support frame 17 to a position (to be referred to as a different imaging position hereinafter) corresponding to the different imaging direction input from the input circuitry 29. The controlling circuitry 31 controls the high voltage generator 11 and the beam limiting device 19 under the X-ray generation conditions to image the object in response to an imaging instruction. Note that the controlling circuitry 31 may rotate the object model in accordance with the different imaging position.

The driving device 23 drives the support frame 17 to move the support frame 17 to the different imaging position in accordance with an instruction from the controlling circuitry 31. The support frame 17 is driven by the driving device 23 to move to the different imaging position. In response to the input of an imaging instruction from the controlling circuitry 31, the high voltage generator 11 applies a tube voltage to the X-ray tube 13 and supplies a tube current to the X-ray tube 13 to image the object from the different imaging direction under the X-ray generation conditions.

The calculation circuitry 35 calculates entrance skin doses in the different imaging direction based on the X-ray generation conditions, the different imaging position, and the like in response to X-ray imaging in the different imaging direction. The calculation circuitry 35 outputs the entrance skin doses in the different imaging direction to the image generation circuitry 25.

The image generation circuitry 25 generates an X-ray image (to be referred to as a different direction image hereinafter) in the different imaging direction based on an output from the X-ray detector 15 concerning the different imaging position. That is, the image generation circuitry 25 generates a different direction image corresponding to at least one imaging direction different from the imaging direction of the X-ray image. Note that the different direction image may be an image based on an output from one X-ray detector in a biplane structure. The image generation circuitry 25 outputs the different direction image to the detection circuitry 37.

The detection circuitry 37 detects a positional shift based on the different direction image. The detection circuitry 37 detects a positional shift along the imaging direction of the X-ray image by, for example, performing registration between the different direction image and the rotated object image. That is, the detected positional shift becomes a positional shift amount in the imaging direction of the X-ray image. The detection circuitry 37 outputs the detected positional shift to the correction circuitry 39.

Assume that an imaging direction concerning an X-ray image is a direction perpendicular to the mount surface of the patient table 21 on which the object P is placed, and an imaging direction concerning a different direction image is a direction parallel to the mount surface of the patient table 21. In this case, the detected positional shift is the positional shift of the object model along the direction perpendicular to the mount surface of the patient table 21.

The correction circuitry 39 corrects a relative positional relationship based on the positional shift amount along the imaging direction. More specifically, the correction circuitry 39 corrects at least one of the size of the display area of entrance skin doses and the size of the object model based on an anatomical landmark on the different direction image so as to match the display area of the entrance skin doses on the object model with the X-ray irradiation range.

For example, correcting the relative positional relationship by the correction circuitry 39 corresponds to enlarging/reducing the size of the object model or the size of the X-ray irradiation range (the display area of the entrance skin doses corresponding to irradiation with X-rays) on the object model.

Note that as in the first embodiment, based on the positional shift amount detected by the detection circuitry 37, the correction circuitry 39 may move the object model or the display area of the entrance skin doses so as to minimize the positional shift amount.

The display 41 corrects and displays the relative positional relationship of the object model or the display area of the entrance skin doses in accordance with the correction result obtained by the correction circuitry 39. More specifically, the display 41 corrects at least one of the size of the object model and the size of the display area of the entrance skin doses, and displays the resultant dose image.

According to the above arrangement, the following effects can be obtained.

The X-ray diagnostic apparatus 1 according to this modification can generate a plurality of X-ray images respectively corresponding to a plurality of different imaging directions by rotating (shaking) the support frame 17 concerning the object P, and can detect a three-dimensional positional shift based on the plurality of generated X-ray images. This allows the X-ray diagnostic apparatus 1 according to the modification to detect a positional shift more accurately, thereby improving the accuracy of the shape of an object model concerning the object P and the accuracy of the display area of entrance skin doses.

(Second Modification)

A difference from the first embodiment is that entrance skin doses are calculated by using a corrected relative positional relationship in response to the detection of a positional shift.

The calculation circuitry 35 calculates an X-ray dose corresponding to irradiation of X-rays concerning an X-ray image used for the detection of a positional shift and an X-ray irradiation position on an object model based on a corrected relative positional relationship, X-ray generation conditions, the position of the X-ray tube 13, the position of the patient table 21, and the object model. The calculation circuitry 35 calculates the latest entrance skin doses by adding X-ray dose calculated after the detection of the positional shift to entrance skin doses before the detection of the positional shift in accordance with the irradiation position.

The calculation circuitry 35 according to this modification calculates entrance skin doses between processing in step Sa6 and processing in step Sa7 in the flowchart of FIG. 6. At this time, the corrected relative positional relationship is maintained during an X-ray examination until a new positional shift is detected. When a new positional shift is detected, the relative positional relationship is further corrected. That is, the relative positional relationship is updated as needed in accordance with the detection of a positional shift.

Note that an update log of relative positional relationships and the relative positional relationship used for the calculation of entrance skin doses may be output to the storage circuitry 33. At this time, the storage circuitry 33 stores the update log and the relative positional relationship used for the calculation of the entrance skin doses along the time series of irradiation with X-rays in an X-ray examination. In addition, the storage circuitry 33 stores X-ray generation conditions, the position of the X-ray tube 13, and the position of the patient table 21 at each time of irradiation with X-rays in an X-ray examination.

According to the above arrangement, the following effects can be obtained.

The X-ray diagnostic apparatus 1 according to this modification can calculate, in response to the detection of a positional shift, entrance skin doses accompanying irradiation with X-rays concerning an X-ray image used for the detection of the positional shift by using a corrected relative positional relationship. That is, the X-ray diagnostic apparatus 1 according to the modification can calculate, in response to the detection of a positional shift, entrance skin doses and the display area of the entrance skin doses in consideration of the positional shift.

This allows the X-ray diagnostic apparatus 1 according to this modification to display accurate entrance skin doses at accurate positions on an object model without any cumbersome operation by the operator even if the object P has moved during X-ray imaging. As described above, the X-ray diagnostic apparatus 1 according to the modification can minimize the positional shift between an object model and the actual object P and improve the accuracy of entrance skin doses to be displayed.

(Third Modification)

A difference from the first embodiment is that entrance skin doses are recalculated by using a corrected relative positional relationship and the time interval input via the input circuitry 29, in response to the detection of a positional shift, in the interval from the time going back from the positional shift detection time by the input time interval to the positional shift detection time.

The input circuitry 29 inputs a time interval for recalculation of entrance skin doses upon going back from the positional shift detection time (to be referred to as the positional shift time hereinafter) in accordance with an instruction from the operator. Note that the time point when a time interval is input is not limited to the positional shift time, the time during an X-ray examination on an object, or the like, and can be input at an arbitrary time. Note that a time interval concerning the recalculation of entrance skin doses may be stored in the storage circuitry 33 in advance.

The calculation circuitry 35 recalculates the above entrance skin doses during a period from the time going back from the time when a positional shift is detected by the detection circuitry 37 by the time interval to the detection time. More specifically, in response to the detection of the positional shift, the calculation circuitry 35 specifies the time (to be referred to as the recalculation start time hereinafter) going back from the positional shift time by the time interval. The calculation circuitry 35 reads out, from the storage circuitry 33, a corrected relative positional relationship during a period from a recalculation start time to a positional shift time, X-ray generation conditions, the position of the X-ray tube 13, the position of the patient table 21, and an object model (to be referred to as dose recalculation information hereinafter).

The calculation circuitry 35 recalculates entrance skin doses at each time of irradiation with X-rays and the display area of the entrance skin doses by using dose recalculation information over a period from the recalculation start time to the positional shift time. The calculation circuitry 35 outputs the recalculated entrance skin doses and the recalculated display area of the entrance skin doses to the storage circuitry 33 and the display 41. The calculation circuitry 35 calculates entrance skin doses and the display area of the entrance skin doses by using the recalculated entrance skin doses and the recalculated display area of the entrance skin doses at irradiation with X-rays after the positional shift time.

The display 41 displays the recalculated entrance skin doses on the object model by using the display area of the entrance skin doses in correspondence with the positional shift time. The calculation circuitry 35 according to this modification recalculates entrance skin doses, for example, in the interval between processing in step Sa6 and processing in step Sa7 in the flowchart of FIG. 6.

Note that an update log of relative positional relationships and the relative positional relationship used for the calculation of entrance skin doses may be output to the storage circuitry 33. In this case, the storage circuitry 33 stores the update log and the relative positional relationship used for the calculation of relative positional relationships along the time series of irradiation with X-rays in an X-ray examination.

(Dose Recalculation Function)

The dose recalculation function is a function of recalculating entrance skin doses or the like during a period from the recalculation start time to the positional shift time in accordance with the detection of a positional shift. Processing associated with the dose recalculation function will be referred to as dose recalculation processing hereinafter.

Figure 9:
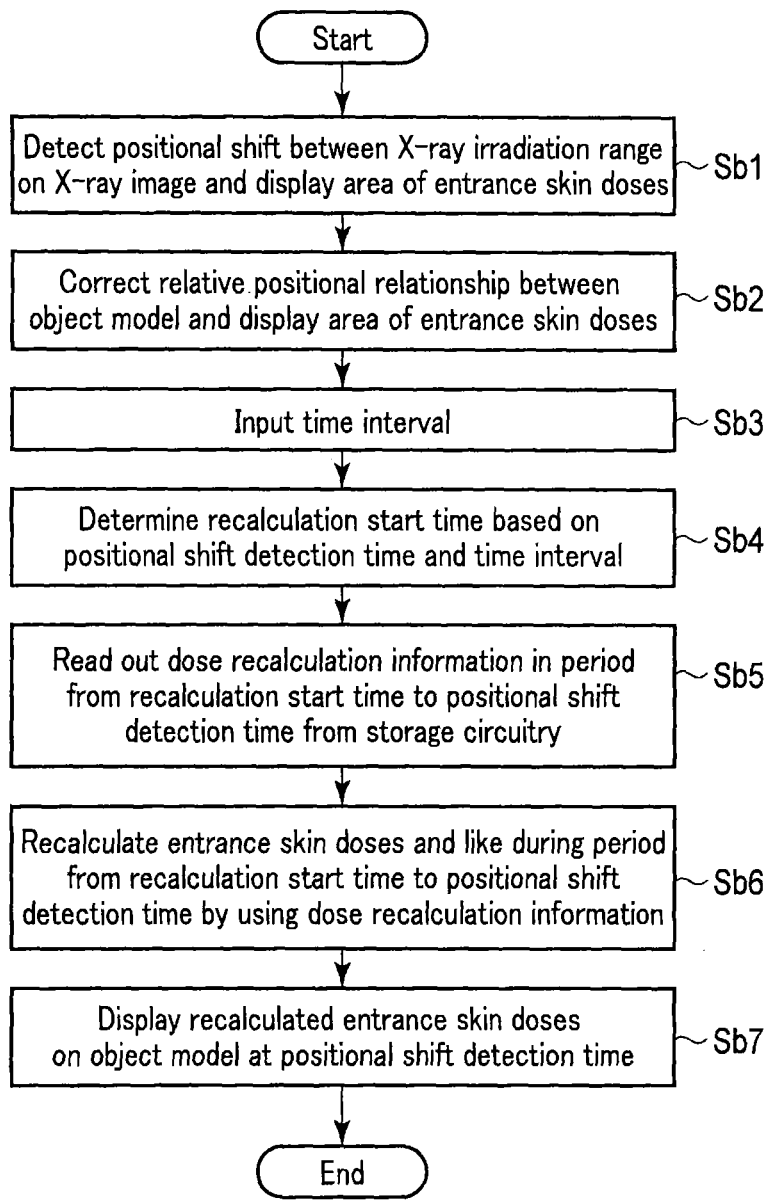
FIG. 9 is a flowchart showing a procedure for dose recalculation processing according to the third modification of the first embodiment.

FIG. 9 is a flowchart showing an example of a procedure for dose calculation processing.

The positional shift between an X-ray irradiation range on an X-ray image and the display area of entrance skin doses is detected (step Sb1). The relative positional relationship between the object model and the display area of the entrance skin doses is corrected (step Sb2). A time interval is input via the input circuitry 29 (step Sb3). A recalculation start time is determined based on the positional shift detection time and the time interval (step Sb4). That is, a recalculation start time is determined by subtracting the time interval from the positional shift time.

Dose recalculation information during a period from the recalculation start time to the positional shift time is read out from the storage circuitry 33 (step Sb5). Entrance skin doses and the display area of the entrance skin doses are recalculated at each irradiation with X-rays by using dose recalculation information over a period from the recalculation start time to the positional shift time (step Sb6). At this time, entrance skin doses corresponding to irradiation with X-rays during a period from the recalculation start time and the positional shift time and the display area of the entrance skin doses are stored in the storage circuitry 33. The stored entrance skin doses and the display area of the entrance skin doses are used for further dose recalculation processing and the reproduction of dose display over an X-ray examination. The entrance skin doses at the positional shift time are displayed on the object model (step Sb7).

According to the above arrangement, the following effects can be obtained.

The X-ray diagnostic apparatus 1 according to this modification can recalculate, in response to the detection of a positional shift, entrance skin doses during a period from the past recalculation start time to the positional shift detection time in an X-ray examination on the object P. This allows the X-ray diagnostic apparatus 1 according to the modification to recalculate entrance skin doses upon going back to the time point when the operator determines the occurrence of a positional shift even when the object P has moved during X-ray imaging. As described above, the X-ray diagnostic apparatus 1 according to the modification can improve the accuracy of entrance skin doses to be displayed upon going back to the past.

(Fourth Modification)

A difference from the first embodiment is that an object model is generated based on volume data concerning an object, and entrance skin doses are recalculated by using the generated object model.

The storage circuitry 33 stores a plurality of three-dimensional object models schematically indicating the object P. Note that the storage circuitry 33 may store past volume data concerning each of a plurality of patients. Volume data are data generated by various types of modalities such as an X-ray CT apparatus and an MRI apparatus, and are transmitted from the modalities to the storage circuitry 33 via, for example, a network and the interface 27.

The input circuitry 29 inputs an instruction (to be referred to as a volume imaging instruction hereinafter) to start volume imaging in accordance with an instruction from the operator during the execution of an X-ray examination on the object P. In this case, volume imaging corresponds to rotation imaging for acquiring projection images of the object P for the reconstruction of volume data. Note that the input circuitry 29 may input X-ray generation conditions (e.g., an imaging range and the rotation range of the support frame 17) concerning volume imaging. The input circuitry 29 outputs the X-ray generation conditions and the volume imaging instruction to the controlling circuitry 31. The input circuitry 29 inputs a selection instruction to select past volume data concerning the object P. The input circuitry 29 outputs the selection instruction to the controlling circuitry 31.

The controlling circuitry 31 outputs an instruction to move the support frame 17 over the rotation range input from the input circuitry 29 to the driving device 23. The controlling circuitry 31 controls the high voltage generator 11 and the beam limiting device 19 under the X-ray generation conditions to perform volume imaging of the object in response to the volume imaging instruction.

The controlling circuitry 31 selects past volume data concerning the object P in accordance with the selection instruction output from the input circuitry 29. The controlling circuitry 31 reads out the selected past volume data from the storage circuitry 33 and outputs the data to the image generation circuitry 25.

The driving device 23 drives the support frame 17 to rotate the support frame 17 within the rotation range in accordance with an instruction from the controlling circuitry 31. The support frame 17 is driven by the driving device 23 to rotate within the rotation range. The high voltage generator 11 applies a tube voltage to the X-ray tube 13 and supplies a tube current to the X-ray tube 13 to execute volume imaging under the X-ray generation conditions in response to the input of an imaging instruction from the controlling circuitry 31.

The image generation circuitry 25 generates a plurality of X-ray images (to be referred to as projection images hereinafter) respectively corresponding to a plurality of X-ray irradiation positions in the rotation range. The plurality of projection images may be stored in the storage circuitry 33 in correspondence with a plurality of imaging direction around the object. The image generation circuitry 25 reconstructs volume data based on the plurality of projection images generated within the rotation range. The image generation circuitry 25 outputs the reconstructed volume data to the storage circuitry 33.

Note that an image reconstruction apparatus (not shown) may execute reconstruction of volume data. As an image reconstruction algorithm, there may be used any of the existing image reconstruction algorithms including analytical image reconstruction methods such as the FBP (filtered back projection) method and the CBP (convolution back projection) method and statistical image reconstruction methods such as the ML-EM (maximum likelihood expectation maximization) method and the OS-EM (ordered subset expectation maximization) method.

The image reconstruction apparatus includes, as hardware resources, a processing device (processor) such as a CPU, MPU, or GPU and a storage device (memory) such as a ROM or RAM. In addition, the image reconstruction apparatus may be implemented by an ASIC, FPGA, CPLD, and SPLD. The processing device implements an image reconstruction function by reading out and executing a program stored in the storage device.

The image generation circuitry 25 generates an object model (measurement image) having measurement data concerning the object P as an object image based on the volume data (the selected past volume data or reconstructed volume data) concerning the object P. If the volume data covers the whole body of the object P, the generated measurement image is an object model (measurement model) having measurement data covering the whole body of the object.

More specifically, the image generation circuitry 25 generates a measurement model having three-dimensional measurement data by using various types of rendering processing. In this case, the three-dimensional measurement data includes, for example, a skin region (edges, sizes, and outer shapes) and organs highly sensitive to X-rays (the crystalline lens, the thyroid gland, and the like).

If the volume data is a portion of the object P, the image generation circuitry 25 selects an object model most suitable for the volume data. The object model most suitable for the volume data is, for example, an object model most similar to the edge and shape of a portion of the object.

That is, the shape and edge of the selected object model is most similar to those of the volume data at a partial region of the object P which corresponds to the volume data. The selection of an object model is executed by, for example, the calculation of a statistical distance such as the degree of similarity after registration processing between the data of the object model and the volume data.

The image generation circuitry 25 then generates an object image (partial measurement model) having three-dimensional measurement data by using the selected object model and the volume data. More specifically, the image generation circuitry 25 extracts, from the selected object model, a partial object model indicating a portion except for a portion of the object P which corresponds to the volume data. The image generation circuitry 25 combines the data of the partial object mode and the volume data to generate a combined image, as an object image (partial measurement model), which is a combination of the object model and the volume data.

The image generation circuitry 25 outputs the measurement model or partial measurement model to the storage circuitry 33, the calculation circuitry 35, the detection circuitry 37, the correction circuitry 39, the display 41, and the like.

The display 41 displays the measurement model upon replacing the object image displayed in advance in response to the generation of the measurement image. The display 41 displays the partial measurement model upon replacing the object image displayed in advance in response to the generation of the combined image. With this operation, the region of the object model corresponding to the volume data is displayed as, for example, a skin region based on the measurement data. Note that the display 41 may display a measurement model or partial measurement model as an object image from the start time of the dose display function in an X-ray examination.

The detection circuitry 37 may detect a positional shift by using volume data and an X-ray image. For example, when volume imaging is executed during an X-ray examination on the object P, the detection circuitry 37 detects the presence/absence of a positional shift by using reconstructed volume data. The detection of a positional shift complies with, for example, the first embodiment, the first modification, and the like.

The correction circuitry 39 corrects the relative positional relationship between an object image and the display area of entrance skin doses on an object model based on volume data. For example, the correction circuitry 39 corrects the relative positional relationship between a measurement image (measurement model) and the display area of entrance skin doses on the measurement image based on an anatomical landmark on an X-ray image and an anatomical landmark on the measurement image. The correction circuitry 39 corrects the relative positional relationship between a combined image (partial measurement model) and the display area of entrance skin doses on the combined image based on an anatomical landmark on an X-ray image and an anatomical landmark on the combined image.

The calculation circuitry 35 recalculates, in response to the generation of a measurement image (measurement model), entrance skin doses during a period from the start time of irradiation of the object P with X-rays to the current time based on X-ray generation conditions, an X-ray irradiation range, the measurement image, a corrected positional relationship, and the position of the X-ray tube 13 concerning the patient table 21. The calculation circuitry 35 recalculates, in response to the generation of a combined image (partial measurement model), entrance skin doses during a period from the start time of irradiation of the object P with X-rays to the current time based on X-ray generation conditions, an X-ray irradiation range, the combined image, a corrected positional relationship, and the position of the X-ray tube 13 concerning the patient table 21.

That is, the calculation circuitry 35 recalculates, in response to the generation of a measurement model (or a partial measurement model), entrance skin doses at each time of irradiation with X-rays and the display area of the entrance skin doses based on the measurement model (or the partial measurement model) and dose recalculation information over a period from the time point of irradiation with X-rays in the past prior to the current time in an X-ray examination (or the first time of irradiation with X-rays) to the current time. Note that the calculation circuitry 35 calculates, in response to the detection of a positional shift, an X-ray dose corresponding to irradiation with X-rays concerning an X-ray image used for the detection of the positional shift and an X-ray irradiation position on a measurement model or partial measurement model based on a corrected relative positional relationship, X-ray generation conditions, the position of the X-ray tube 13, the position of the patient table 21, and the measurement model or partial measurement model.

The calculation circuitry 35 outputs the recalculated entrance skin doses and the recalculated display area of the entrance skin doses to the storage circuitry 33 and the display 41. The calculation circuitry 35 calculates entrance skin doses and the display area of the entrance skin doses at irradiation with X-rays, after the generation of a measurement image or combined image, by using the recalculated entrance skin doses, the recalculated display area of the entrance skin doses, and the measurement model or partial measurement model.

(Dose Recalculation Function)

The dose recalculation function according to this modification is a function of recalculating entrance skin doses at each time of irradiation with X-rays and the display area of the entrance skin doses over a period from irradiation with X-rays at the start time of an X-ray examination to the current time in response to the generation of a measurement model or partial measurement model. The following is processing associated with the dose recalculation function (dose recalculation processing) when volume data is generated by rotating the C-arm around the object during an X-ray examination on the object P.

Figure 10:
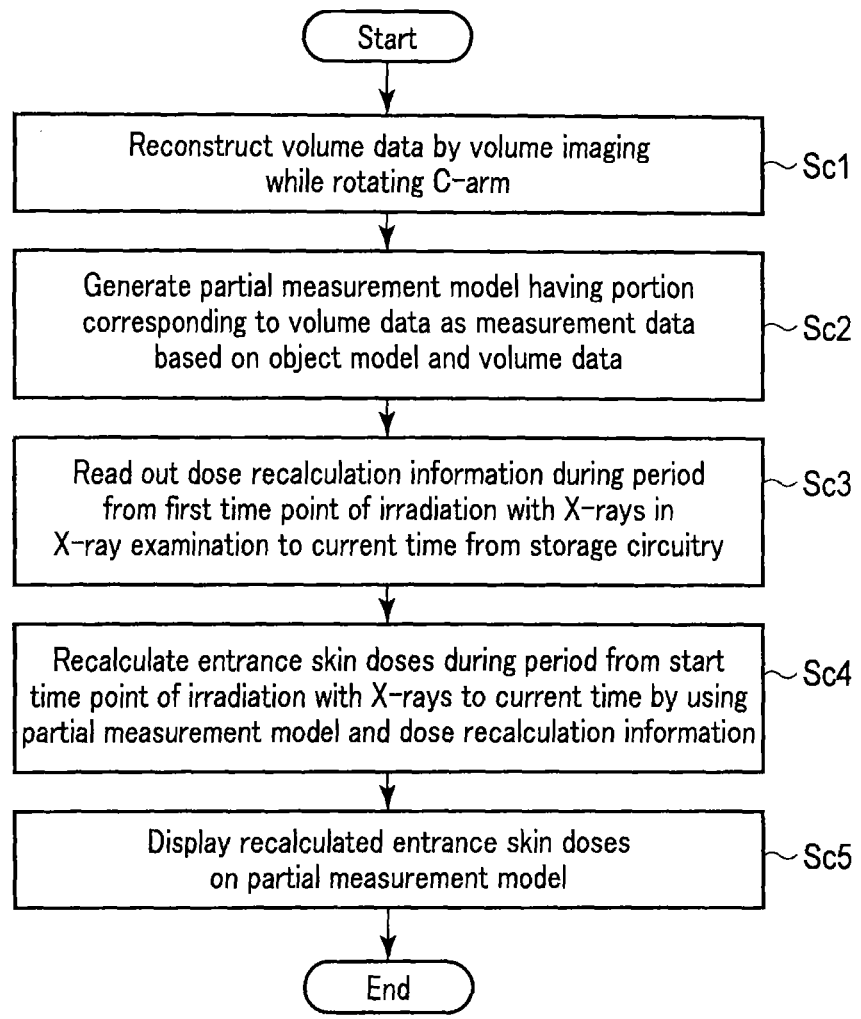
FIG. 10 is a flowchart showing a procedure for dose recalculation processing according to the fourth modification of the first embodiment.

FIG. 10 is a flowchart showing an example of a procedure for dose recalculation processing according to this modification. The dose recalculation processing according to the modification can be arbitrarily executed as long as, for example, it is executed between processing in step Sa3 and processing in step Sa8 in the flowchart of FIG. 6.

An instruction to perform volume imaging is input via the input circuitry 29 in an X-ray examination on the object P. The support frame (C-arm) 17 is rotated around the object to execute X-ray imaging and generate a plurality of projection images. Volume data is reconstructed based on the plurality of projection images (step Sc1). An object model most suitable for the volume data is selected based on the volume data.

In this case, a non-overlapping region which does not overlap the volume data is specified on the selected object model. A partial measurement model having a portion corresponding to the volume data as measurement data is generated based on the non-overlapping region on the object model and the volume data (step Sc2).

Dose recalculation information during a period from the time point of irradiation with X-rays in the past prior to the current time (or the first time point of irradiation with X-rays) in an X-ray examination to the current time (the input time of an instruction to perform volume imaging), i.e., the information used for the calculation of entrance skin doses and the like at each time of irradiation with X-rays in an X-ray examination, is read out from the storage circuitry 33 (step Sc3). Entrance skin doses during a period from the start time point of irradiation with X-rays to the current time and the display area of the entrance skin doses are recalculated at each time of irradiation with X-rays based on the partial measurement model and dose recalculation information (step Sc4).

The recalculated entrance skin doses are superimposed and displayed on the partial measurement model. Note that if an instruction to select past volume data concerning the object P is input, processing in step Sc2 and the subsequent steps is executed. At this time, in step Sc2, a measurement model is generated.

FIG. 11 is a view showing volume data S, an object model T, and a partial measurement model U. The volume data S is generated accompanying volume imaging with respect to an object. Entrance skin doses are superimposed on the object model T until immediately before the volume imaging. The partial measurement model U has measurement data V as a portion, which is based on the volume data S. That is, according to this modification, on an object model, measurement data is assigned to a portion of the object model obtained by volume imaging.

According to the above arrangement, the following effects can be obtained.

The X-ray diagnostic apparatus 1 according to this modification generates a measurement model or partial measurement model in accordance with the input of a volume imaging instruction or an instruction to select past volume data, and recalculates entrance skin doses during a period from the start time point of irradiation with X-rays to the current time and the display area of the entrance skin doses at each time of irradiation with X-rays by using the generated measurement model or partial measurement model.

This allows the X-ray diagnostic apparatus 1 according to this modification to generate a measurement model or partial measurement model corresponding to the accurate outer shape (edge) of the object P, concerning the object model used by the dose display function, based on the volume data of the object P. In addition, entrance skin doses can be recalculated by using the measurement model or partial measurement model. As described above, the X-ray diagnostic apparatus 1 according to this modification can improve the accuracy of entrance skin doses to be displayed upon going back to the past.

Second Embodiment

A difference from the first embodiment is that an object model most matching the outer shape of the object P during an X-ray examination is specified from a plurality of object models, and entrance skin doses are recalculated by using the specified object model. An X-ray diagnostic apparatus according to the second embodiment will be described below with reference to the accompanying drawings. Note that the same reference numerals in the following description denote constituent elements having almost the same functions and arrangements, and a repetitive description will be made only when required.

Figure 12:
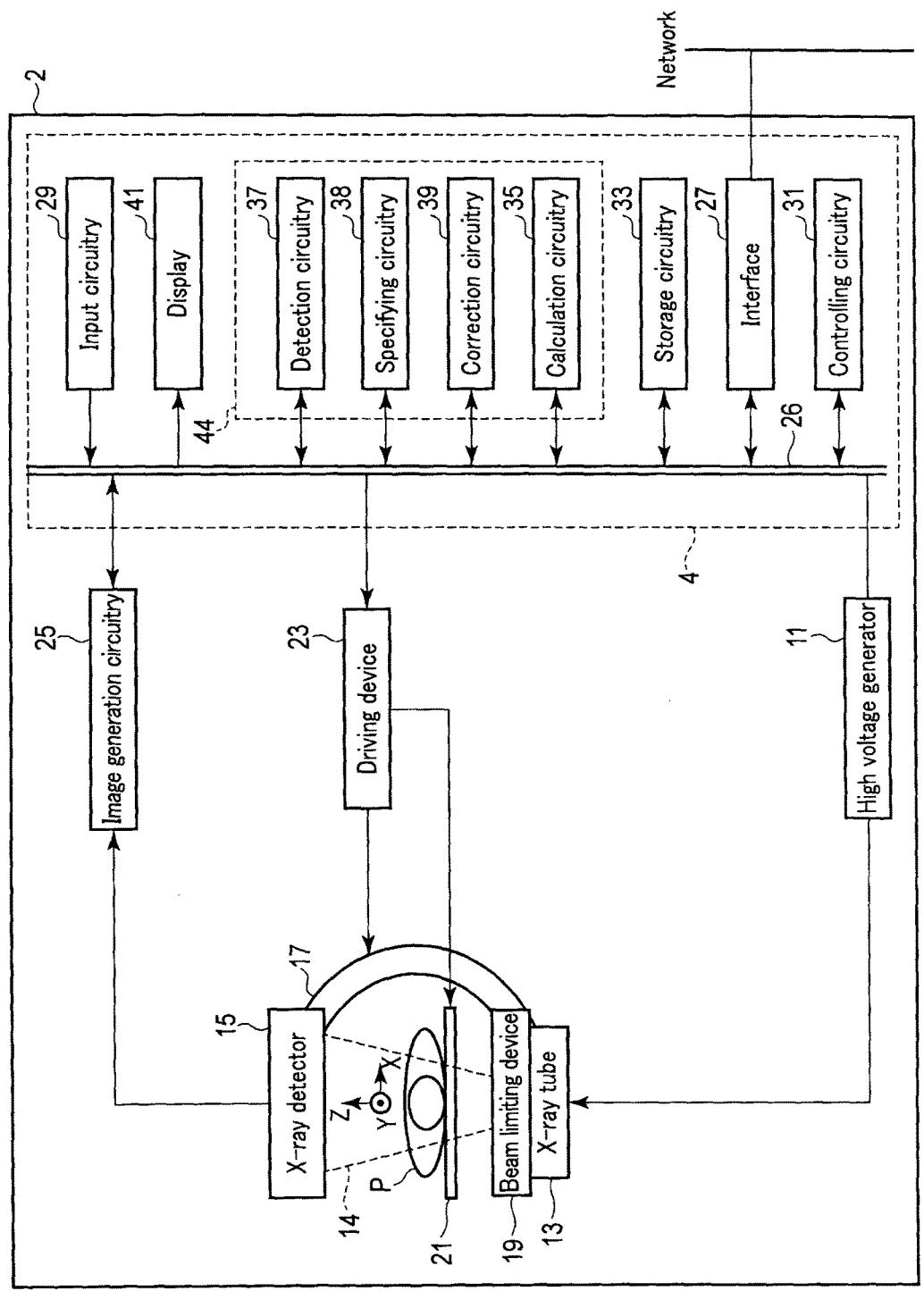
FIG. 12 is a block diagram showing an example of the arrangement of an X-ray diagnostic apparatus according to the second embodiment.

FIG. 12 is a block diagram showing an example of the arrangement of an X-ray diagnostic apparatus 2 according to this embodiment.

Storage circuitry 33 stores a plurality of three-dimensional object models schematically indicating an object as object images. Note that the storage circuitry 33 may store past volume data respectively corresponding to a plurality of patients. In addition, the storage circuitry 33 may store volume data reconstructed by volume imaging with respect to an object P.

Detection circuitry 37 detects the outer shape (edge) of an object on volume data or an X-ray image by, for example, edge detection. The detection circuitry 37 outputs the detected outer shape to specifying circuitry 38.

The specifying circuitry 38 specifies an object model as an object image which matches the outer shape of an object from a plurality of object models based on the object model on which entrance skin doses are superimposed and an X-ray image. More specifically, the specifying circuitry 38 performs registration between the outer shape detected on an X-ray image and the outer shape of each of a plurality of object models to specify an object mode matching the outer shape of the object from the plurality of object models.

Note that the specifying circuitry 38 may specify an object model based on the input of an instruction to change an object model via input circuitry 29. In addition, the specifying circuitry 38 may specify an object model by using reconstructed volume data or past volume data. In this case, the specifying circuitry 38 specifies an object model matching the outer shape of the object from a plurality of object models by registration between the outer shape detected in the reconstructed volume data or the outer shape detected in the past volume data and the outer shape of each of the plurality of object models.

The specifying circuitry 38 is a processor which has processing circuitry and reads out and executes a program for specifying an object model from the storage circuitry 33, thereby implementing a function corresponding to the readout program. According to the above description, the single processing circuitry executes the object model specifying function. However, a plurality of independent processors may be combined to form processing circuitry, and the respective processors may execute programs to implement the respective types of functions.

The word "processor" used in the above description means circuitry such as a CPU, GPU, ASIC, SPLD, CPLD, or FPGA. Note that it is possible to directly incorporate programs in the circuitry of the processor instead of storing them in the storage circuitry 33. In this case, the processor implements various types of functions by reading out programs incorporated in the circuitry and executing them.

In addition, the function for specifying the object model corresponds to the correction of the relative positional relationship between the display area of entrance skin doses and an object image (object model) in a broad sense, and hence the specifying circuitry 38 may be incorporated in correction circuitry 39. Furthermore, each processor (calculation circuitry 35, the detection circuitry 37, the specifying circuitry 38, and the correction circuitry 39) in this embodiment may be formed as one processor by combining a plurality of independent circuits to implement various types of functions as well as being formed as single circuitry for each processor. In addition, the plurality of constituent elements in FIG. 2 may be integrated into one processor (a processing device 44 in FIG. 2) to implement the corresponding function.

The calculation circuitry 35 recalculates, in response to the specifying of an object model, entrance skin doses during a period from the start time point of irradiation of an object with X-rays in an X-ray examination to the current time and the display area of the entrance skin doses based on the specified object model, an X-ray irradiation range, X-ray generation conditions, a corrected positional relationship, and the position of an X-ray tube 13 concerning a patient table 21.

More specifically, the calculation circuitry 35 recalculates, in response to the specifying of an object model, entrance skin doses at each time of irradiation with X-rays and the display area of the entrance skin doses based on the specified object model and dose recalculation information over a period from the time point of irradiation with X-rays in the past prior to the current time (or the first time point of irradiation with X-rays) in an X-ray examination to the current time. The calculation circuitry 35 outputs the recalculated entrance skin doses and the recalculated display area of the entrance skin doses to the storage circuitry 33 and a display 41.

At irradiation with X-rays after the object model is specified, the calculation circuitry 35 calculates entrance skin doses and the display area of the entrance skin doses by using the recalculated entrance skin doses, the recalculated display area of the entrance skin doses, and the specified object model.

According to the above arrangement, the following effects can be obtained.

The X-ray diagnostic apparatus 2 according to this embodiment can specify an object model matching the outer shape of the object P from a plurality of object models based on an instruction from the operator, an X-ray image, and the volume data reconstructed by volume imaging or past volume data, and can recalculate entrance skin doses during a period from the start time point of irradiation with X-rays in an X-ray examination to the current time and the display area of the entrance skin doses based on the specified object model and dose recalculation information. As described above, the X-ray diagnostic apparatus 2 according to this embodiment can specify an object model most matching the outer shape of the object and improve the accuracy of entrance skin doses to be displayed upon going back to the past.

Third Embodiment

A difference from the first and second embodiments is that when X-ray CT is performed with respect to an object P after an X-ray examination on the object P, the relative positional relationship is corrected by using the volume data reconstructed by X-ray CT, and entrance skin doses and the like are recalculated based on the corrected positional relationship and dose recalculation information.

This embodiment will exemplify a medical image processing apparatus including a plurality of constituent elements 3 enclosed by the dotted line in FIG. 1 or a plurality of constituent elements 4 enclosed by the dotted line in FIG. 12. Note that the embodiment may exemplify a medical image diagnostic apparatus such as an X-ray CT apparatus or MRI apparatus which includes the plurality of constituent elements 3 enclosed by the dotted line in FIG. 1 or the plurality of constituent elements 4 enclosed by the dotted line in FIG. 12 and can generate volume data. Note that the same reference numerals in the following description denote constituent elements having almost the same functions and arrangements, and a repetitive description will be made only when required.

Input circuitry 29 inputs an instruction (to be referred to as a recalculation instruction hereinafter) to recalculate entrance skin doses. The input circuitry 29 inputs an instruction (to be referred to as a moving display instruction hereinafter) to display recalculated entrance skin doses as a moving image.

Storage circuitry 33 stores the volume data reconstructed accompanying X-ray CT or the like executed with respect to the object P after an X-ray examination. Note that if this embodiment is an X-ray CT apparatus, a reconstruction device may output volume data to calculation circuitry 35, detection circuitry 37, and correction circuitry 39. The storage circuitry 33 stores, concerning an X-ray examination on the object P, X-ray generation conditions, an X-ray irradiation range, the position of an X-ray tube 13 concerning a patient table 21, and the relative positional relationship between an object model and the display area of entrance skin doses on the object model.

The controlling circuitry 31 controls the calculation circuitry 35, the detection circuitry 37, the correction circuitry 39, and the like to recalculate entrance skin doses in response to the input of a recalculation instruction. The controlling circuitry 31 controls a display 41 to display the recalculated entrance skin doses as a moving image in response to the input of a moving image display instruction.

The detection circuitry 37 detects a positional shift by using volume data at each of a plurality of times of irradiation with X-rays in an X-ray examination. More specifically, the detection circuitry 37 detects the positional shift caused by the movement of the object P at each of a plurality of times of irradiation with X-rays in an X-ray examination by comparing volume data with an object model. The detection circuitry 37 outputs the detected positional shift to the correction circuitry 39, together with the X-ray irradiation time.

The correction circuitry 39 corrects a relative positional relationship at each of a plurality of times of irradiation with X-rays in an X-ray examination by using volume data. For example, the correction circuitry 39 corrects the relative positional relationship between an object model and the display area of entrance skin doses on the object model to reduce a detected positional shift based on an anatomical landmark in the volume data and an anatomical landmark on the object model. The correction circuitry 39 outputs the relative positional relationship corrected at each of a plurality of times of irradiation with X-rays in an X-ray examination to the calculation circuitry 35.

The calculation circuitry 35 recalculates entrance skin doses during a period from the first irradiation with X-rays to the last irradiation with X-ray in an X-ray examination and the display area of the entrance skin doses at each irradiation with X-ray over a period during which the X-ray examination is executed, based on X-ray generation conditions, an X-ray irradiation range, an object model, a corrected positional relationship, and the position of the X-ray tube 13 concerning the patient table 21. The calculation circuitry 35 outputs the recalculated entrance skin doses and the recalculated display area of the entrance skin doses to the storage circuitry 33 and the display 41, together with the X-ray irradiation times in the X-ray examination.

The display 41 superimposes the recalculated entrance skin doses on the display area of the object model and displays the resultant image as a moving image along the X-ray irradiation times by using the corrected positional relationship in response to the input of a moving image display instruction.

(Recalculation Moving Image Display Function)

A recalculation moving image display function is a function of recalculating entrance skin doses over a period of an X-ray examination by using the volume data and the like reconstructed accompanying X-ray CT after the X-ray examination on the object P, superimposing the recalculated entrance skin doses on an object model, and displaying the resultant image as a moving image. Processing associated with the recalculation moving image display function (to be referred to as recalculation moving image processing hereinafter) will be described below.

Figure 13:
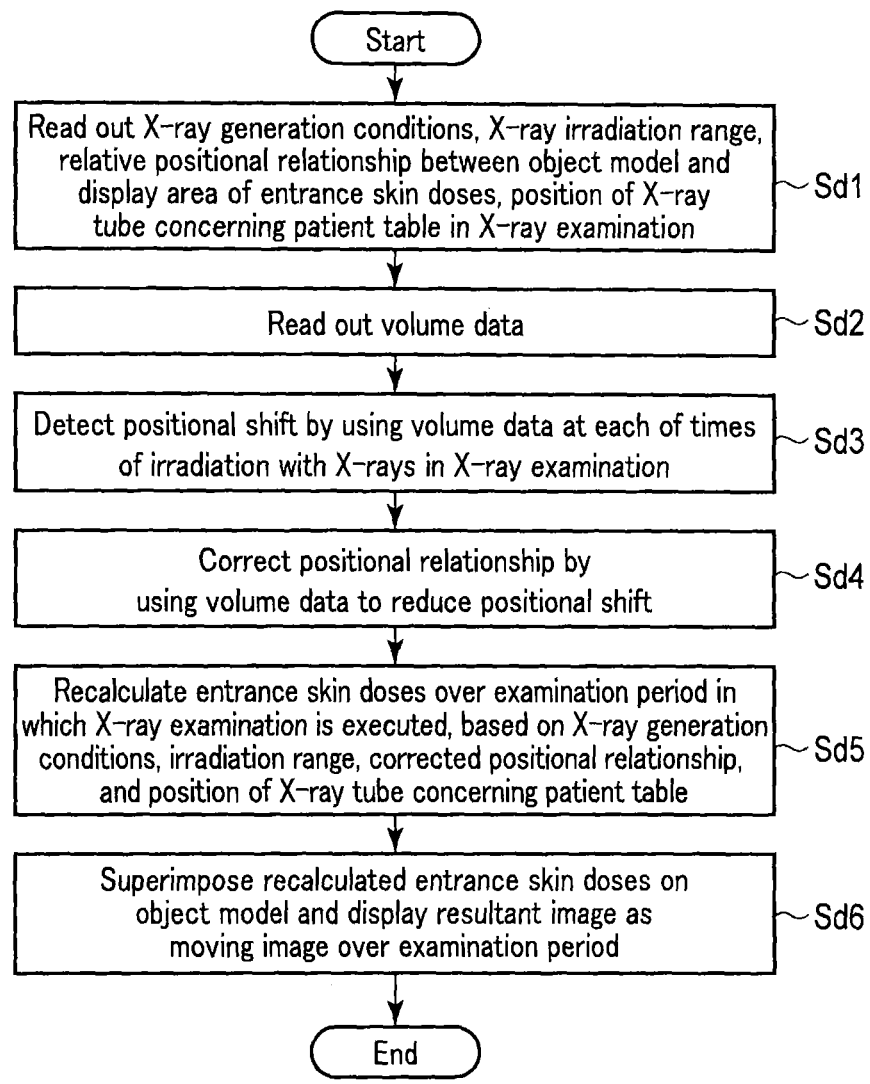
FIG. 13 is a flowchart showing a procedure for dose recalculation processing according to the third embodiment.

FIG. 13 is a flowchart showing an example of a procedure for recalculation moving image processing.

A recalculation instruction is input in accordance with an instruction from the operator via the input circuitry 29. X-ray generation conditions in an X-ray examination, an X-ray irradiation range, the relative positional relationship between an object model and the display area of entrance skin doses, and the position of the X-ray tube 13 concerning the patient table 21 are read out from the storage circuitry 33 (step Sd1).

The volume data reconstructed via the reconstruction device and the like in the X-ray CT apparatus is read out from the storage circuitry 33 (step Sd2). Note that if this medical image processing device is mounted in an X-ray CT apparatus or MRI apparatus, processing in step Sd2 is the processing of reconstructing volume data by using a reconstruction device.

A positional shift is detected by using the volume data at each of a plurality of times of irradiation with X-rays in an X-ray examination (step Sd3). The relative positional relationship is corrected by using the volume data so as to reduce the positional shift (step Sd4). Entrance skin doses and the display area of the entrance skin doses are recalculated at each time of irradiation with X-rays over an examination period during which an X-ray examination is executed, based on X-ray generation conditions, an irradiation range, a corrected positional relationship, and the position of the X-ray tube 13 concerning the patient table 21 (step Sd5).

A moving image display instruction is input in accordance with an instruction from the operator via the input circuitry 29. The moving image obtained by superimposing the recalculated entrance skin doses on an object model is displayed on the display 41 over an examination period.

According to the above arrangement, the following effects can be obtained.

The medical image processing apparatus or medical image diagnostic apparatus according to this embodiment can correct a relative positional relationship by using the volume data acquired after an X-ray examination (e.g., the volume data reconstructed by an X-ray CT apparatus or MRI apparatus), and can recalculate entrance skin doses and the like based on the corrected positional relationship and dose recalculation information. This allows the medical image processing apparatus or medical image diagnostic apparatus according to the embodiment to recalculate entrance skin doses with higher accuracy even after an X-ray examination and display the resultant image as a moving image, thereby contributing to a reduction in total incident dose and a reduction in local incident dose.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A medical image diagnostic apparatus, comprising:
an X-ray tube configured to irradiate an object with X-rays;
an X-ray detector configured to detect the X-rays;
processing circuitry configured to generate an X-ray image based on the detected X-rays; and
a display configured to display an incident dose region, which illustrates an incident dose distribution of the X-rays on the object, superimposed on an object image indicating the object,
wherein the processing circuitry is further configured to correct, based on the generated X-ray image, a relative positional relationship between the object image and the incident dose region that is superimposed on the object image.

2. The apparatus according to claim 1, wherein the processing circuitry is further configured to correct at least one of a position and a size of the object image based on an anatomical landmark in the X-ray image.

3. The apparatus according to claim 1, wherein the processing circuitry is further configured to
generate a different direction image corresponding to an imaging direction different from in imaging direction of the X-ray image, and
correct at least one of a size of the incident dose region and a size of the object image based on an anatomical landmark in the different direction image.

4. The apparatus according to claim 1, wherein the processing circuitry is further configured to:
detect a positional shift between an irradiation range of the X-rays and the incident dose region, and
calculate the incident dose distribution based on an X-ray generation condition concerning generation of the X-rays, the irradiation range of the X-rays, the corrected positional relationship, and a position of the X-ray tube with respect to a patient table, in response to detection of the positional shift.

5. The apparatus according to claim 4, further comprising input circuitry configured to input a predetermined time interval concerning recalculation of the incident dose distribution,
wherein the processing circuitry is further configured to recalculate the incident dose distribution during a period defined from a previous time that is prior to a detection time of the positional shift by the time interval, to the detection time.

6. The apparatus according to claim 1, wherein the object image is a three-dimensional object model schematically indicating the object and having an anatomical landmark, and
the processing circuitry is further configured to correct at least one of a position and a size of the object image based on an anatomical landmark in the X-ray image and an anatomical landmark in the object model.

7. The apparatus according to claim 6, wherein the processing circuitry is further configured to
detect a positional shift between an anatomical landmark of a predetermined organ in the X-ray image and an anatomical landmark of the predetermined organ in the object model, and
calculate the incident dose distribution based on the positional relationship corrected based on the positional shift, an irradiation range of the X-ray, an X-ray generation condition concerning generation of the X-rays, and a position of the X-ray tube with respect to a patient table, in response to detection of the positional shift.

8. The apparatus of claim 7, wherein the processing circuitry is further configured to correct at least one of a position and a size of the object model by rotating the object model based on the positional shift.

9. The apparatus according to claim 1, further comprising:
a memory storing a plurality of three-dimensional object models schematically indicating the object, wherein the processing circuitry is further configured to
specify, as the object image, an object model matching a size of the object, from the object models, based on the X-ray image and the object image; and
recalculate the incident dose distribution at a past time prior to a current time in an X-ray examination on the object based on the specified object model, an irradiation range of the X-ray, an X-ray generation condition concerning generation of the X-rays, the corrected positional relationship, and a position of the X-ray tube with respect to a patient table, in response to specifying of the object model.

10. The apparatus according to claim 9, wherein the size of the object corresponds to an outer shape of the object.

11. The apparatus according to claim 1, further comprising:
a memory storing a plurality of three-dimensional object models schematically indicating an object; and
input circuitry configured to input a change of the object model,
wherein the processing circuitry is further configured to
recalculate the incident dose distribution at a past time prior to a current time in an X-ray examination on the object based on the changed object model, an irradiation range of the X-ray, an X-ray generation condition concerning generation of the X-rays, the corrected positional relationship, and a position of the X-ray tube with respect to a patient table, in response to a change of the object model.

12. The apparatus according to claim 1, further comprising:
a memory storing a plurality of three-dimensional object models schematically indicating the object and past volume data corresponding to each of a plurality of patients;
input circuitry configured to input a change instruction for past volume data concerning the object in the past volume data, wherein the processing circuitry is further configured to
specify, as the object image, an object model matching an outer shape of the object, from the object models, based on volume data corresponding to the change instruction and the object image, and
recalculate the incident dose distribution of a past time prior to a current time in an X-ray examination on the object based on the specified object model, an irradiation range of the X-ray, an X-ray generation condition concerning generation of the X-rays, the corrected positional relationship, and a position of the X-ray tube with respect to a patient table.

13. The apparatus according to claim 1, wherein the processing circuitry is further configured to generate volume data based on a plurality of X-ray images acquired by rotating the X-ray tube and the X-ray detector around the object while making the X-ray tube and the X-ray detector face each other, and
the apparatus further comprises
a memory storing a plurality of three-dimensional object models schematically indicating the object as the object image, wherein the processing circuitry is further configured to
specify, as the object image, an object model matching an outer shape of the object from the object models, based on the volume data and the object image, and
recalculate the incident dose distribution at a past time prior to a current time in an X-ray examination on the object based on the specified object model, an irradiation range of the X-ray, an X-ray generation condition concerning generation of X-rays, the corrected positional relationship, and a position of the X-ray tube with respect to the patient table, in response to specifying of the object model.

14. The apparatus according to claim 1, wherein the processing circuitry is further configured to generate, as the object image, a three-dimensional measurement image having measurement data concerning the object, based on volume data of the object,
the display is configured to display the measurement image in place of the object image, in response to generation of the measurement image, and
the processing circuitry is further configured to correct a relative positional relationship between the measurement image and the incident region dose on the measurement image based on the volume data.

15. The apparatus according to claim 14, wherein the processing circuitry is further configured to recalculate the incident dose distribution at a past time prior to a current time in an X-ray examination on the object based on an X-ray generation condition concerning generation of the X-rays, an irradiation range of the X-ray, the measurement image, the corrected positional relationship, and a position of the X-ray tube with respect to a patient table, in response to generation of the measurement image.

16. The apparatus according to claim 15, wherein when the measurement image is an image indicating a portion of the object, the processing circuitry is configured to generate, as the object image, a combined image obtained by combining a three-dimensional object model indicating a portion different from the portion indicated with the measurement image, and
the display is configured to display the combined image in place of the object image, in response to generation of the combined image.

17. The apparatus according to claim 15, wherein the volume data comprises at least one of
data reconstructed by X-ray computed tomography or magnetic resonance imaging with respect to the object, and
data reconstructed based on a plurality of X-ray images acquired by rotating, around the object, a support frame which supports the X-ray tube and the X-ray detector so as to make the X-ray tube and the X-ray detector face each other.

18. The apparatus according to claim 1, wherein the X-ray image comprises real-time fluoroscopic images sequentially generated by the processing circuitry.

19. The apparatus according to claim 1, wherein the incident dose distribution comprises an entrance skin dose distribution on the object.

20. A medical image diagnostic apparatus, comprising:
a memory storing an X-ray generation condition concerning generation of X-rays irradiated to an object, an irradiation range of the X-rays concerning the object, a position of an X-ray tube with respect to a patient table, a relative positional relationship between an object image indicating the object and an incident dose region illustrating an incident dose distribution superimposed on the object image, and volume data acquired after an X-ray examination on the object;

processing circuitry configured to
  correct the positional relationship by using the volume data;
  recalculate the incident dose distribution over a period during which the X-ray image is executed, based on the X-ray generation condition, the irradiation range, the corrected positional relationship, and the position of the X-ray tube; and
a display configured to superimpose the recalculated incident dose distribution on the object image by using the corrected positional relationship over the period, and display the image as a moving image.

* * * * *